(12) United States Patent
Hessler et al.

(10) Patent No.: US 9,629,624 B2
(45) Date of Patent: *Apr. 25, 2017

(54) CIRCULAR SURGICAL STAPLER WITH MATING ANVIL AND SHELL ASSEMBLY

(71) Applicant: Covidien LP, Mansfield, MA (US)

(72) Inventors: Thomas R. Hessler, Bethel, CT (US); Keith Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 995 days.

This patent is subject to a terminal disclaimer.

(21) Appl. No.: 13/848,292

(22) Filed: Mar. 21, 2013

(65) Prior Publication Data

US 2013/0214027 A1 Aug. 22, 2013

Related U.S. Application Data

(63) Continuation of application No. 13/542,471, filed on Jul. 5, 2012, now Pat. No. 8,424,535, which is a
(Continued)

(51) Int. Cl.
| | | |
|---|---|---|
| *A61B 17/068* | (2006.01) |
| *A61B 17/115* | (2006.01) |
| *A61B 17/11* | (2006.01) |
| *A61B 1/31* | (2006.01) |
| *A61B 17/02* | (2006.01) |

(Continued)

(52) U.S. Cl.
CPC .......... *A61B 17/068* (2013.01); *A61B 17/115* (2013.01); *A61B 17/1114* (2013.01); *A61B 1/31* (2013.01); *A61B 17/02* (2013.01); *A61B 17/0469* (2013.01); *A61B 17/1155* (2013.01); *A61B 17/32053* (2013.01);
(Continued)

(58) Field of Classification Search
CPC ... A61B 19/00; A61B 17/068; A61B 17/0684; A61B 17/0686; A61B 17/1155
USPC ........................................................ 227/179.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

Canadian Office Action dated Sep. 14, 2015, issued in Canadian Application No. 2,684,146.
(Continued)

*Primary Examiner* — Gloria R Weeks

(57) ABSTRACT

A surgical stapler comprising a handle assembly, an elongated body portion extending distally from the handle assembly, and a head portion disposed adjacent a distal portion of the elongated body portion and including an anvil assembly and a shell assembly. The anvil assembly is movable in relation to the shell assembly between spaced and approximated positions. The anvil assembly has an anvil head and a plurality of projections extending proximally of the anvil head, the projections engageable with a portion of the shell assembly.

18 Claims, 29 Drawing Sheets

Related U.S. Application Data continuation of application No. 12/582,064, filed on Oct. 20, 2009, now Pat. No. 8,231,042.

(60) Provisional application No. 61/111,759, filed on Nov. 6, 2008.

(51) Int. Cl.
  *A61B 17/04* (2006.01)
  *A61B 17/3205* (2006.01)
  *A61B 17/00* (2006.01)
  *A61B 17/072* (2006.01)
  *A61B 90/00* (2016.01)

(52) U.S. Cl.
  CPC .............. *A61B 2017/00818* (2013.01); *A61B 2017/0725* (2013.01); *A61B 2017/1142* (2013.01); *A61B 2090/061* (2016.02)

(56) References Cited

U.S. PATENT DOCUMENTS

| | | | |
|---|---|---|---|
| 3,552,626 A | 1/1971 | Astafiev | |
| 3,606,888 A | 9/1971 | Wilkinson | |
| 3,638,652 A | 2/1972 | Kelley | |
| 3,771,526 A | 11/1973 | Rudie | |
| 4,198,982 A | 4/1980 | Fortner et al. | |
| 4,207,898 A * | 6/1980 | Becht | A61B 17/115 227/179.1 |
| 4,289,133 A | 9/1981 | Rothfuss | |
| 4,304,236 A * | 12/1981 | Conta | A61B 17/115 227/179.1 |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,610,383 A * | 9/1986 | Rothfuss | A61B 17/07207 227/176.1 |
| 4,617,928 A * | 10/1986 | Alfranca | A61B 10/04 227/180.1 |
| 4,633,874 A * | 1/1987 | Chow | A61B 17/07207 227/176.1 |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,307,976 A * | 5/1994 | Olson | A61B 17/07207 227/175.3 |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,452,837 A * | 9/1995 | Williamson, IV | A61B 17/07207 227/176.1 |
| 5,454,825 A | 10/1995 | Van Leeuwen et al. | |
| 5,464,415 A | 11/1995 | Chen | |
| 5,465,894 A * | 11/1995 | Clark | A61B 17/072 227/175.1 |
| 5,470,006 A | 11/1995 | Rodak | |
| 5,474,223 A | 12/1995 | Viola et al. | |
| 5,485,947 A * | 1/1996 | Olson | A61B 17/07207 227/176.1 |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,605,272 A * | 2/1997 | Witt | A61B 17/072 227/175.2 |
| 5,609,285 A | 3/1997 | Grant et al. | |
| 5,626,591 A | 5/1997 | Kockerling et al. | |
| 5,630,539 A * | 5/1997 | Plyley | A61B 17/07207 227/175.1 |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |

(56) References Cited

U.S. PATENT DOCUMENTS

| | | | |
|---|---|---|---|
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 6,988,649 B2 * | 1/2006 | Shelton, IV ..... A61B 17/07207 227/175.2 |
| 6,988,650 B2 * | 1/2006 | Schwemberger .... A61B 17/072 227/176.1 |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,097,089 B2 * | 8/2006 | Marczyk .......... A61B 17/07207 227/175.2 |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,210,609 B2 | 5/2007 | Leiboff et |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 * | 9/2008 | Bilotti ................. A61B 17/115 227/179.1 |

(56) References Cited

U.S. PATENT DOCUMENTS

| | | |
|---|---|---|
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,832,612 B2* | 11/2010 | Baxter, III ....... A61B 17/07207 227/175.1 |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,123,103 B2 | 2/2012 | Milliman |
| 8,141,763 B2 | 3/2012 | Milliman |
| 8,181,838 B2 | 5/2012 | Milliman et al. |
| 8,348,122 B2 | 1/2013 | Milliman et al. |
| 8,464,924 B2 | 6/2013 | Gresham et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2005/0184123 A1* | 8/2005 | Scirica ................. A61B 17/072 227/176.1 |
| 2005/0236459 A1 | 10/2005 | Gresham |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0210739 A1 | 9/2008 | Milliman et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |

(56) References Cited

U.S. PATENT DOCUMENTS

| | | |
|---|---|---|
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0594436 A2 | 4/1994 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 | 1/1988 |
| WO | WO 8706448 A | 11/1987 |
| WO | WO 8900406 A1 | 1/1989 |
| WO | WO 9006085 A1 | 6/1990 |
| WO | WO 01/54594 | 8/2001 |
| WO | WO2004/032766 | 4/2004 |
| WO | WO2008/107918 | 9/2008 |

OTHER PUBLICATIONS

European Office Action dated Nov. 16, 2015, issued in EP Application No. 09252570.

* cited by examiner

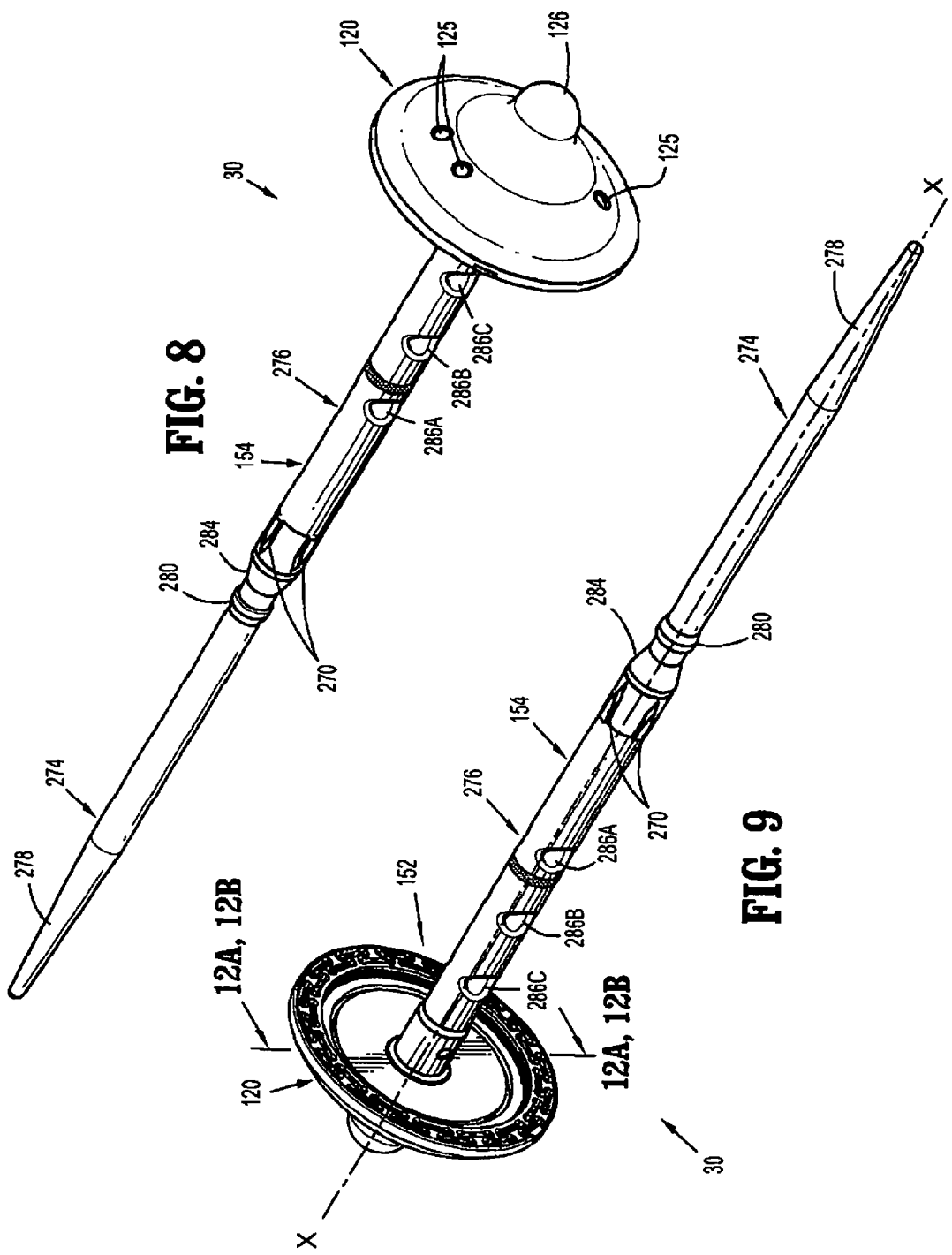

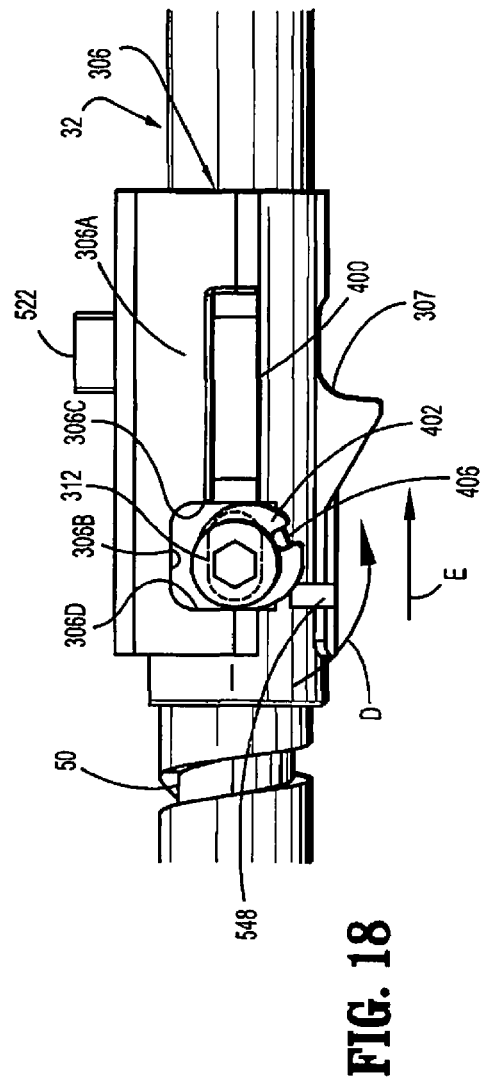
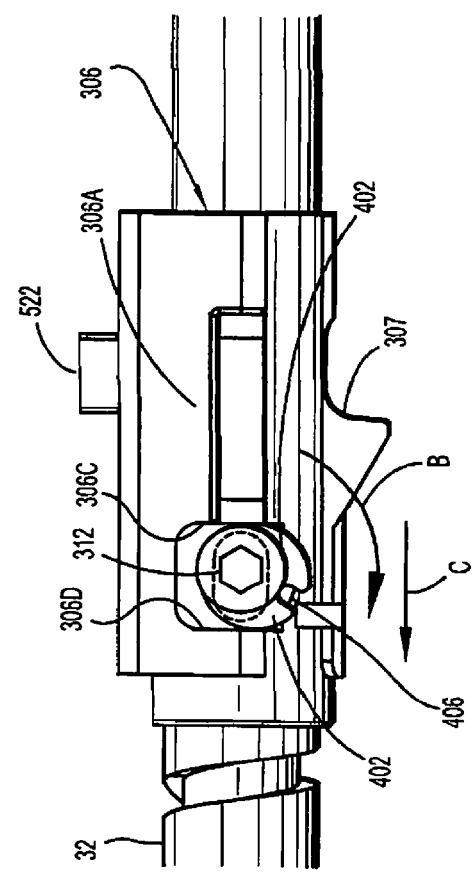
FIG. 18
FIG. 19

CIRCULAR SURGICAL STAPLER WITH MATING ANVIL AND SHELL ASSEMBLY

CROSS-REFERENCE TO RELATED APPLICATIONS

This application is a Continuation of U.S. application Ser. No. 13/542,471 filed Jul. 5, 2012, now patented 8,424,535, which is a Continuation of U.S. application Ser. No. 12/582,064 filed Oct. 20, 2009, now patented 8,231,042, which claims benefit of Provisional application No. 61/111,759 filed Nov. 6, 2008, and the disclosures of each of the above-identified applications are hereby incorporated by reference in their entirety.

BACKGROUND

1. Technical Field

The present disclosure relates generally to surgical stapling devices for applying surgical fasteners to body tissue. More particularly, the present disclosure relates to surgical stapling devices suitable for performing circular anastomosis and/or treating the internal walls of hollow body organs, e.g., hemorrhoidal tissue.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage.

Examples of instruments for performing circular anastomosis of hollow organs are described in U.S. Pat. Nos. 7,303,106, 6,053,390, 5,588,579, 5,119,983, 5,005,749, 4,646,745, 4,576,167, and 4,473,077. Typically, these instruments include an elongated shaft having a handle portion at a proximal end to actuate the instrument and a staple holding component disposed at a distal end. An anvil assembly including an anvil center rod with attached anvil head is mounted to the distal end of the instrument adjacent the staple holding component. Opposed end portions of tissue of the hollow organ(s) to be stapled are clamped between the anvil head and the staple holding component as these components are approximated. The clamped tissue is stapled by driving one or more staples from the staple holding component through the staple slots so that the ends of the staples pass through the tissue and are deformed by anvil pockets of the anvil head. An annular knife is concurrently advanced to core tissue with the hollow organ to free a tubular passage within the organ.

Besides anastomosis of hollow organs, surgical stapling devices for performing circular anastomosis have been used to treat internal hemorrhoids in the rectum. Hemorrhoids are masses of tissue in the anus containing enlarged blood vessels. Internal hemorrhoids are inside the anal canal; external hemorrhoids lie outside the anal canal. In hemorrhoidectomy, the hemorrhoids are removed. Stapled hemorrhoidopexy is a surgical procedure in which the stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply to the tissue, thus causing the hemorrhoids to shrink.

During the use of a circular stapling device for hemorrhoid treatment, the anvil head and the staple holding component of the device are inserted through and into the rectum with the anvil head and the stapling holding component in an open or unapproximated position. Thereafter, a purse string suture is used to pull the internal hemorrhoidal tissue and/or mucosal tissue toward the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

Various techniques of using the purse string suture to pull the internal hemorrhoidal tissue towards the center rod are known in the art. For example, U.S. Pat. No. 6,102,271 to Longo, et al., discusses grasping and pulling the purse string proximally through the use of a separate device that is inserted into the stapling device.

International Application Publication No. WO 2008/107918 to Rebuffat, et al., discloses placing the purse string suture into one or more annular grooves formed in the anvil center rod.

It would be desirable, therefore, to provide a surgical stapling device including structure that is configured and dimensioned to enhance alignment between the staple holding component and anvil head.

It certain procedures, it may be desirable to provide a longer center rod (anvil shaft) of the anvil assembly. Therefore, such enhanced alignment and cooperation between the stapling component and anvil would be advantageous.

SUMMARY

In one aspect of the present disclosure, a surgical stapling device is disclosed that includes a surgical stapler comprising a handle assembly, an elongated body portion extending distally from the handle assembly, and a head portion disposed adjacent a distal portion of the elongated body portion and including an anvil assembly and a shell assembly, the anvil assembly being movable in relation to the shell assembly between spaced and approximated positions. The anvil assembly has an anvil head and a plurality of projections extending proximally of the anvil head, the projections engageable with a portion of the shell assembly.

Preferably, the shell assembly includes a plurality of openings aligning with respective projections of the anvil assembly. In a preferred embodiment, the projections are frictionally received in a respective opening. The projections can have a tapered end.

In one embodiment, the anvil assembly includes an anvil shaft extending proximally of the anvil head and removably mountable to an anvil retainer of the stapler.

In one embodiment, the plurality of projections are substantially equidistantly radially spaced. In one embodiment, the projections extend substantially parallel with the anvil shaft.

In one embodiment, the anvil assembly includes a center rod and an anvil head, the center rod including at least one aperture extending transversely therethrough and the aperture configured and dimensioned to receive a flexible member such that the flexible member extends transversely through the center rod.

In another aspect of the present disclosure an anvil assembly is provided comprising an anvil head and a center rod extending from the anvil head. The center rod includes a first annular engagement member configured to removably engage an anvil retainer of a surgical stapling device. A plurality of projections extend proximally of the anvil head for engagement with a plurality of openings in the surgical stapling device.

The center rod may include a plurality of apertures extending transversely therethrough, the apertures configured and dimensioned to receive a suture therethrough.

In one embodiment, the plurality of projections are substantially equidistantly radially spaced. In one embodiment, the plurality of projections comprises first and second projections spaced approximately 180 degrees apart.

The center rod preferably includes a plurality of splines for alignment of the center rod with a shell assembly of a surgical stapling device with the projections preferably terminating distally of the splines.

BRIEF DESCRIPTION OF THE DRAWINGS

Various embodiments of the present disclosure are described herein below with reference to the drawings, wherein:

FIGS. 8 and 9 are side perspective views of the anvil assembly;

FIG. 16A is cross-sectional view showing engagement of the anvil assembly of FIG. 16 with an alternative embodiment of the shell boss of the shell assembly;

FIGS. 18 and 19 are side views of a screw stop component of the surgical stapling device;

DETAILED DESCRIPTION

Figure 1:
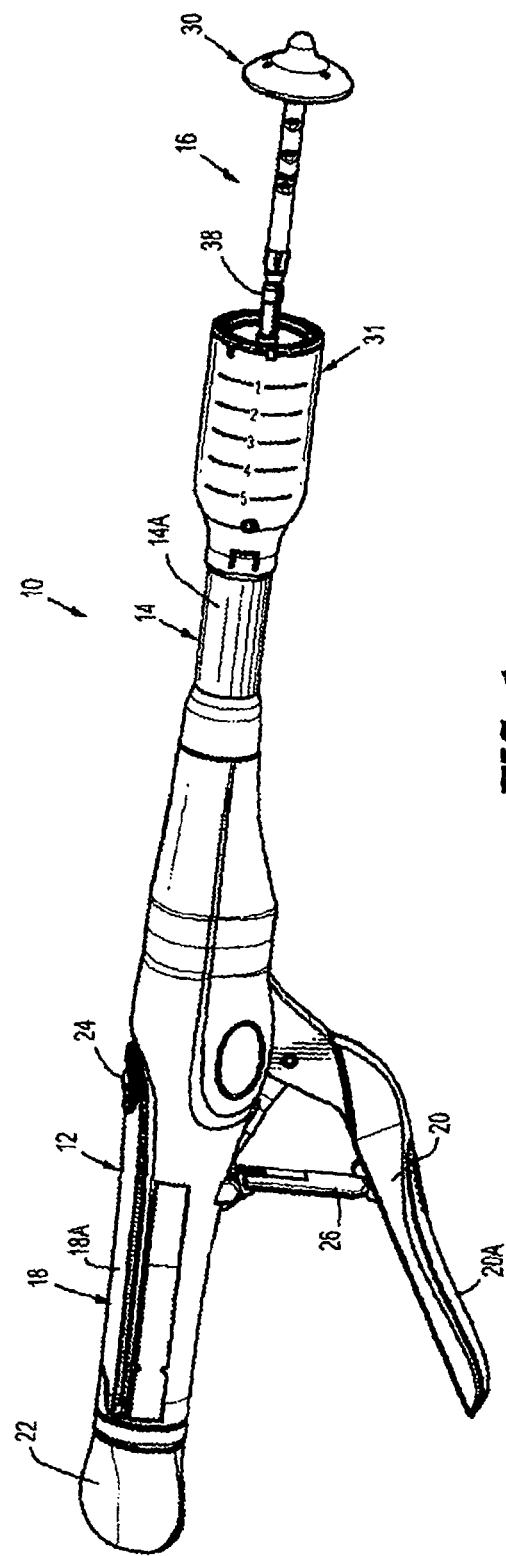
FIG. 1 is a side, perspective view of a surgical stapling device including an anvil assembly and a shell assembly shown in an un-approximated position, in accordance with the principles of the present disclosure.

The presently disclosed surgical stapling device will now be described in detail with reference to the drawings in which like reference numerals designate identical or corresponding elements in each of the several views. Throughout this description, the term "proximal" will refer to the portion of the surgical stapling device, or component thereof, that is closer to the clinician during proper use, and the term "distal" will refer to the portion of the surgical stapling device, or component thereof, that is further from the clinician during proper use. Additionally, the terms "hemorrhoidal tissue" and the like will refer to hemorrhoidal tissue, as well as tissue positioned adjacent to hemorrhoidal tissue, including mucosal tissue. The presently disclosed surgical stapling device is particularly suited for surgical hemorrhoid procedures, although it can be used in other procedures. The term "hemorrhoid procedure" should be understood to encompass surgical hemorrhoidectomies, hemorrhoidopexies, mucosectomies, procedures for the treatment of colon prolapse, and all such related procedures.

FIG. 1 illustrates the presently disclosed surgical stapling device, which is referred to generally by the reference numeral 10. Briefly, the surgical stapling device 10 includes a handle assembly 12, a central body portion 14 including an outer tube 14a, and a distal head portion 16. The handle assembly 12 includes a stationary handle 18, a firing trigger 20, a rotatable approximation knob 22, and an indicator 24 positioned on the stationary handle 18, which provides the clinician with information regarding whether or not the stapling device 10 is ready for firing, i.e. the anvil has been satisfactorily approximated. It is envisioned that the stationary handle 18 may be formed from individual handle sections 19A, 19B (FIG. 2) that together define a housing for the internal components of handle assembly 12. As shown in FIG. 1, the stationary handle 18 and the trigger 20 may respectively include cushioned and slip-resistant portions 18A, 20A to facilitate gripping and manipulation of the handle assembly 12 by the clinician during the surgical procedure. A trigger lock 26 is pivotally mounted to the handle assembly 12, and is selectively repositionable by the clinician to prevent inadvertent firing of the stapling device 10. The structure and operation of the trigger lock 26 will be discussed in detail herein below.

The head portion 16 of the surgical stapling device 10 includes an anvil assembly 30 and a shell assembly 31. Except where otherwise noted, the components of the stapling device 10 are generally formed from thermoplastics including polycarbonates, and metals including stainless steel and aluminum. The particular material selected to form a particular component will depend upon the strength requirements of the particular component. For example, the anvil assembly 30 may be formed from a metal such as stainless steel, whereas portions of handle assembly 12 may be formed from thermoplastic such as a polycarbonate. Alternately, other materials having the requisite strength requirements which are suitable for surgical use may be used to form the components of the stapling device 10.

Figure 36:
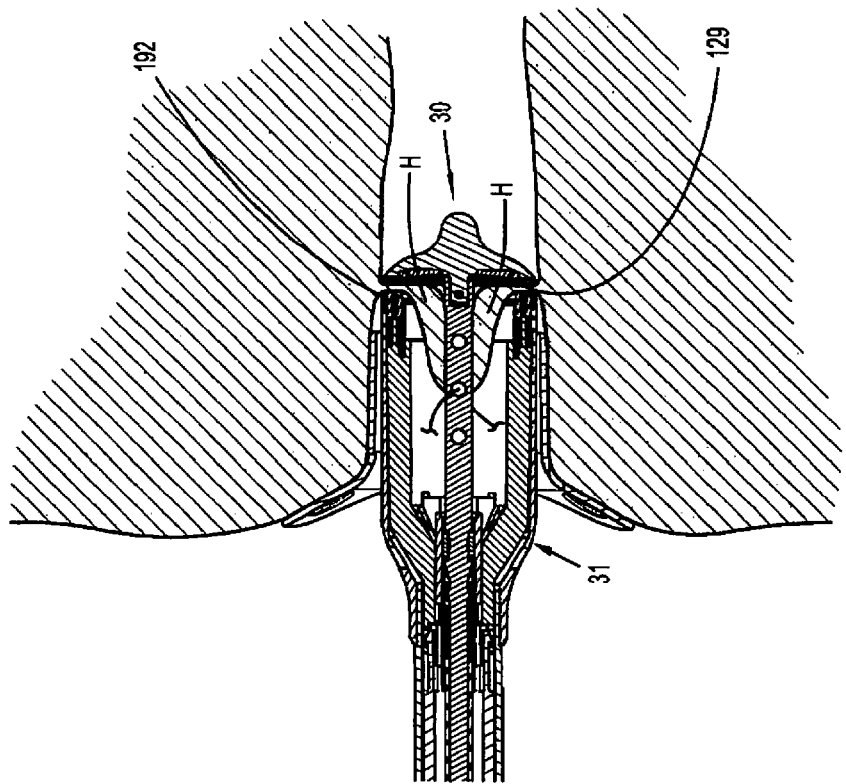
FIG. 36 is a longitudinal cross-sectional view illustrating the distal end of the surgical stapling device positioned within the port component of the anoscope kit following approximation of the anvil assembly and the shell assembly.

The head portion 16 is repositionable between an un-approximated position (FIGS. 1, 13), wherein the anvil assembly 30 is spaced a distance from the shell assembly 31, and an approximated position, wherein the anvil assembly 30 abuts the shell assembly (FIG. 36). To advance and retract the anvil assembly 30 relative to the shell assembly 31, and thus repositioning of the head portion 16 between the un-approximated and approximated positions, the stapling device 10 further includes an approximation mechanism.

Referring now to FIGS. 1-4, the approximation mechanism includes approximation knob 22, a drive screw 32, a rotatable sleeve 33, and an anvil retainer 38 that is configured and dimensioned to securely receive the anvil assembly 30 in a manner that will be described below.

The rotatable sleeve 33 (FIG. 2) includes a substantially cylindrical hollow body portion 40, as well as a substantially cylindrical collar 42, which together define a central bore 33A. The collar 42 includes structure that is configured and dimensioned for engagement with corresponding structure formed on the stationary handle 18 (FIG. 1). For example, in the embodiment illustrated in FIG. 2, the collar 42 includes an annular groove 44 formed thereabout that is configured and dimensioned to receive an inwardly extending flange 46 that is formed on an inner wall of the stationary handle 18. Engagement between the groove 44 and the flange 46 inhibits relative axial movement between the sleeve 33 and the stationary handle 18, while permitting rotation of the sleeve 33 relative to the stationary handle 18.

A proximal end of the body portion 40 of the rotatable sleeve 33 extends through an opening 18b (FIG. 2) located at a proximal end of the stationary handle 18. The body portion 40 also includes one or more ribs 48 that are positioned on the outer surface thereof that are positioned within a pair of internal slots 49A that are formed in the approximation knob 22. Engagement between the ribs 48 and the slots 49A inhibits relative rotation between the sleeve 33 and the approximation knob 22 such that rotation of the approximation knob 22 causes corresponding rotation of the sleeve 33.

Figure 2:
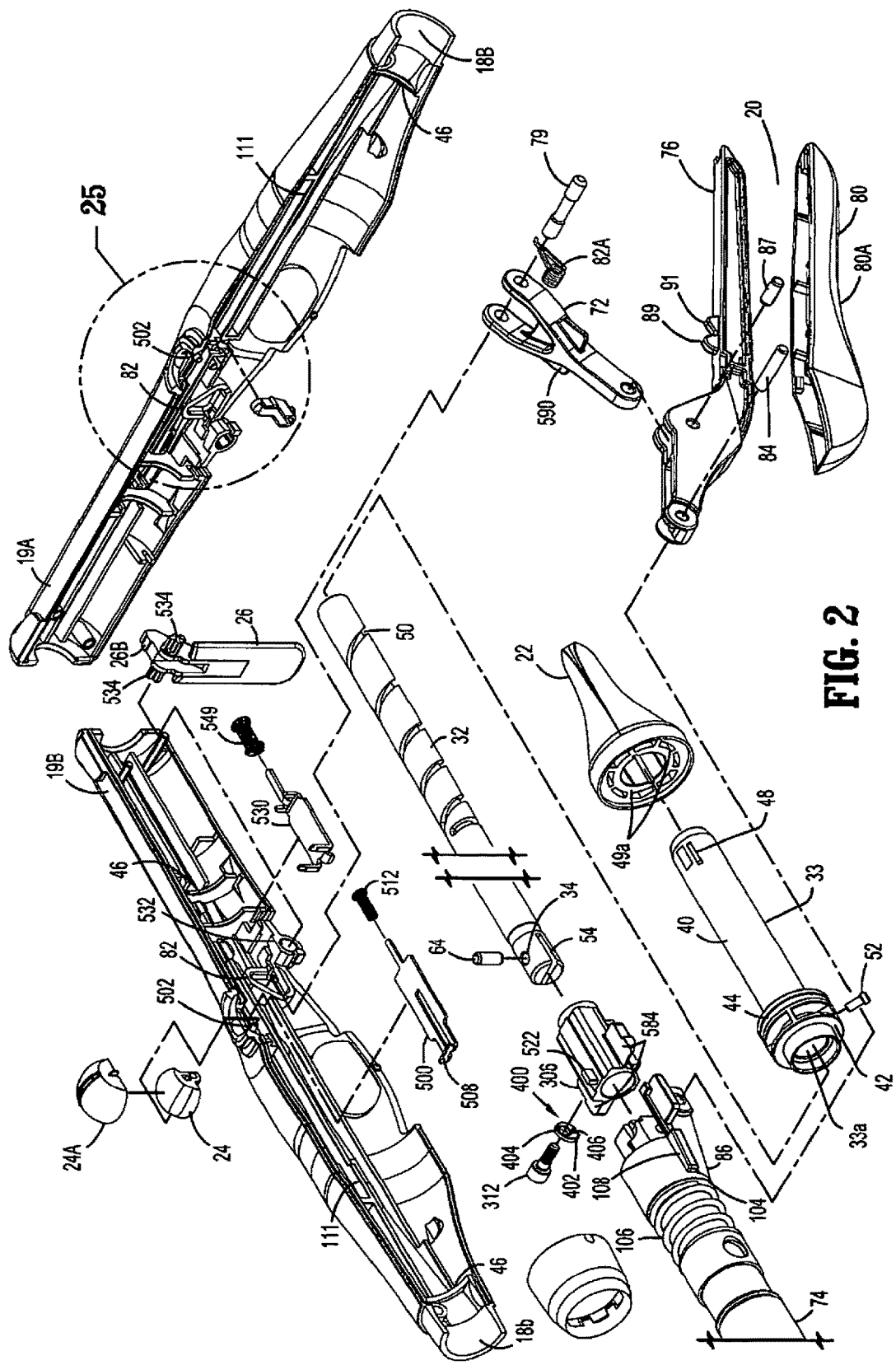
FIG. 2 is an exploded view of a portion of the surgical stapling device of FIG. 1, including the handle assembly.
Figure 3:
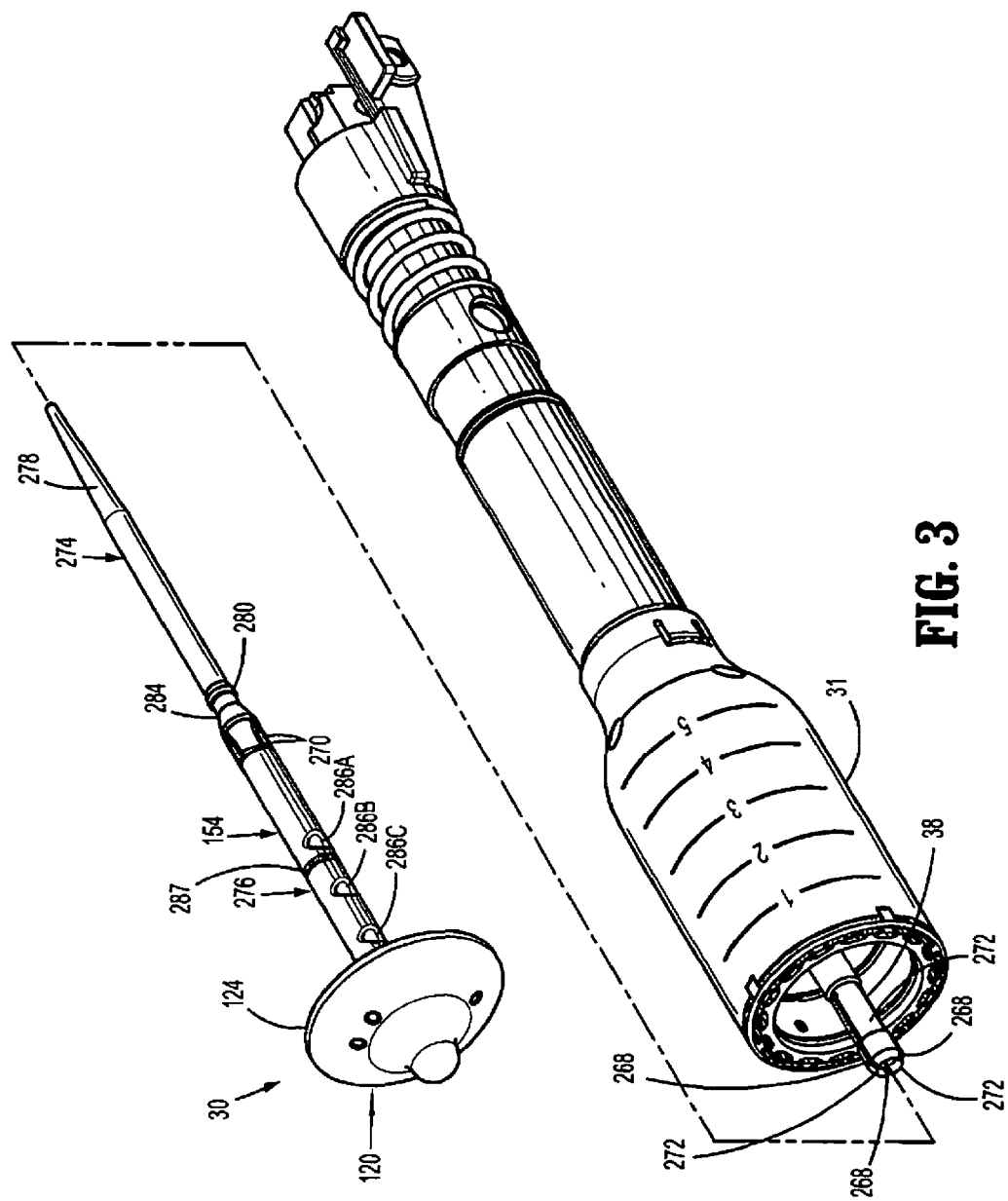
FIG. 3 is a side perspective view of the anvil assembly and the shell assembly of the surgical stapling device.

The drive screw 32 is slidably positioned within the central bore 33A of the rotatable sleeve 33. The screw 32 includes a proximal portion with a helical channel 50 (FIG. 2) that engages with a pin 52 that extends radially through the collar 42 of the sleeve 33. Since the sleeve 33 is axially fixed with respect to the stationary handle 18, rotation of the sleeve 33 about the screw 32 causes the pin 52 to move along the channel 50 of the screw 32 to effect axial movement of the screw 32 within the stationary handle 18. At a distal end, the screw 32 further includes axial grooves 54 and a throughbore 34 that receives a pin 64 (FIG. 2). Although the structure identified by reference numerals 52 and 64 is referred to, and illustrated as, a pin, it should be understood that any structure capable of achieving the disclosed interactions may be employed, e.g., screws, rivets, or the like.

Figure 4:
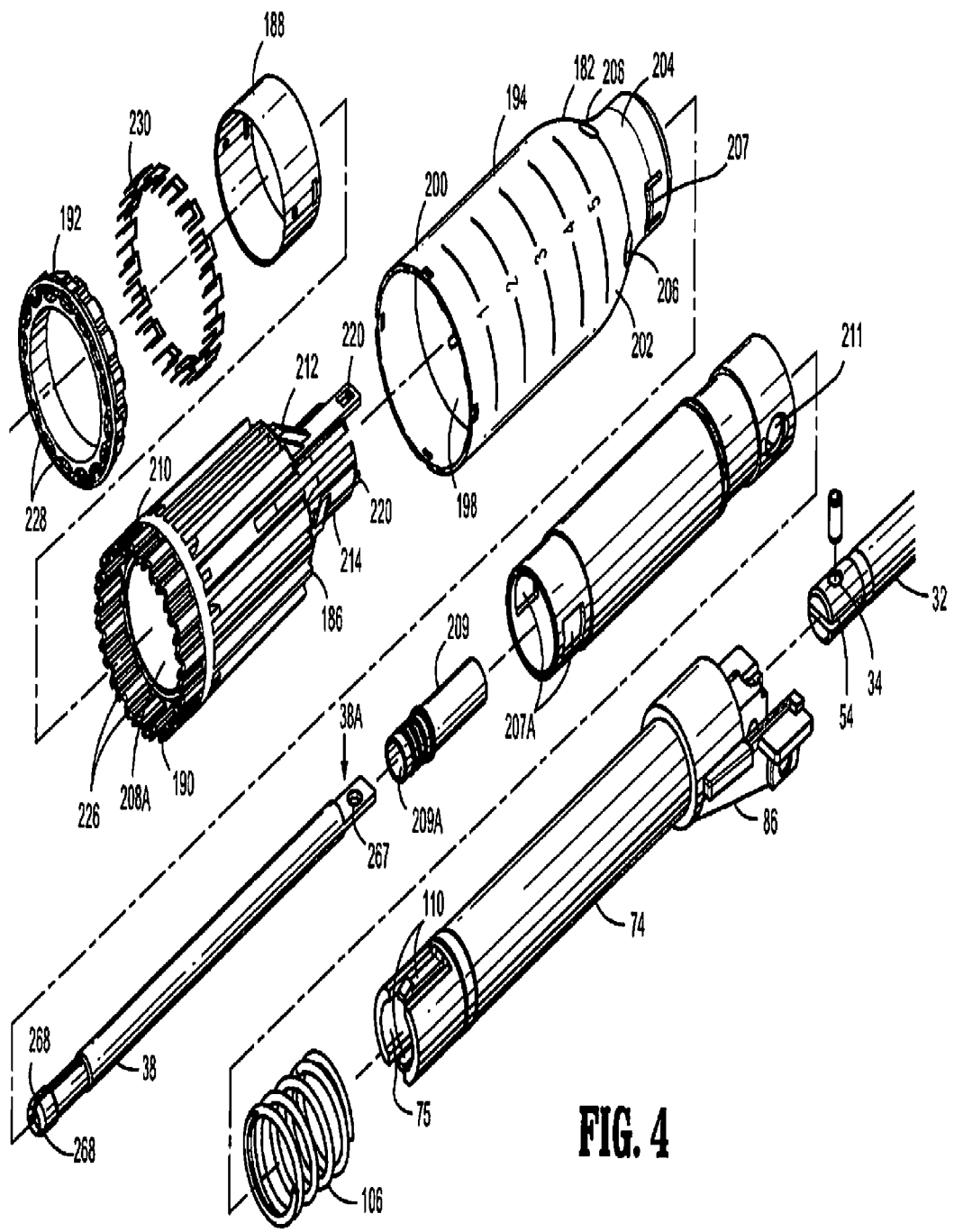
FIG. 4 is an exploded view of the shell assembly.

As seen in FIG. 4, the anvil retainer 38 has a proximal end 38A with a throughbore 267 formed therein. The throughbore 267 receives pin 64 (FIG. 2). The anvil retainer 38 is connected to the screw 32 by positioning the proximal end 38A of the anvil retainer 38 within the axial groove 54 of the screw 32, and the pin 64 within the throughbore 34 of the screw 32 and the throughbore 267 of the anvil retainer 38. The anvil retainer 38 also includes an annular recess to engage the corresponding annular protrusion 280 (FIGS. 3, 10) on the anvil assembly 30, and axial grooves 268 (FIG. 3) that engage a corresponding number of splines 270 formed on a center rod 154 of the anvil assembly 30. The axial grooves 268 separate the anvil retainer 38 into flexible fingers 272. Additional detail regarding engagement of the anvil retainer 38 and the anvil assembly 30 are provided below. It should be appreciated that while the anvil retainer 38 is illustrated as including three fingers 272, and the center rod 154 is illustrated as including three splines 270, the fingers 272 and the splines 270 may be present in greater or fewer numbers in alternative embodiments of the present disclosure.

Figure 5:
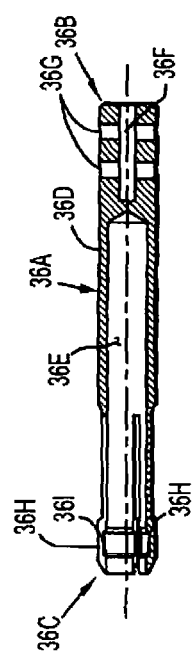
FIG. 5 is a longitudinal cross-sectional view of one embodiment of an anvil retainer for use with the surgical stapling device.
Figure 7:
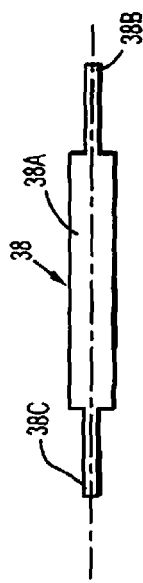
FIG. 7 is a side view of a connector for use with the anvil retainer shown in FIG. 5 to operatively connect the anvil retainer to a drive screw.
Figure 6:
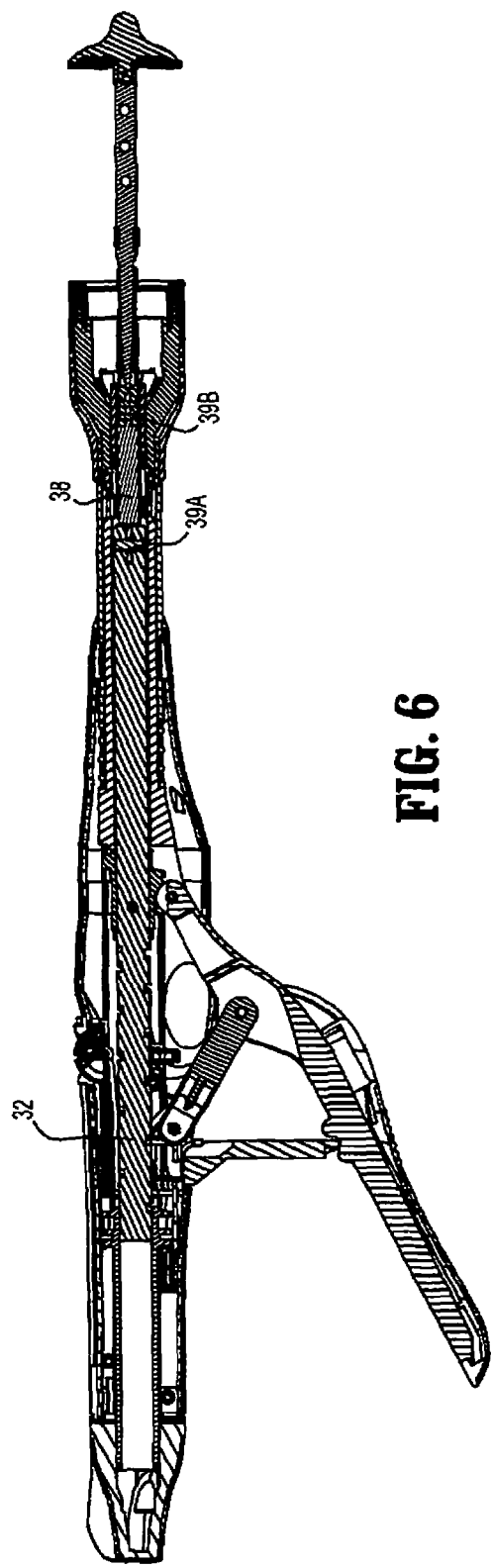
FIG. 6 is a longitudinal cross-sectional view of the surgical stapling device of FIG. 1 incorporating the anvil retainer shown in FIG. 5.

With reference to FIGS. 5-7, in an alternative embodiment of the present disclosure, the stapling device 10 includes an anvil retainer referred to generally by reference character 36A (FIG. 5). The anvil retainer 36A is substantially similar to the anvil retainer 38 described above, and accordingly, will only be discussed with respect to any differences therefrom.

The anvil retainer 36A has respective proximal and distal ends 36B, 36C, and includes a body 36D defining an elongated bore 36E. The proximal end 36B of the body 36D includes a longitudinal slot 36F, as well as a pair of transverse throughbores 36G, and the distal end 36C of the body 36D includes segmented, flexible arms 36H. Although illustrated as including three segmented arms 36G, the segmented arms may be present in greater or fewer numbers in additional embodiments of the anvil retainer 36A. Each arm 36G includes an inner retention surface 36I that is configured and dimensioned to engage the anvil assembly 30 (FIGS. 1, 3) to inhibit relative movement therebetween. Specifically, the inner retention surface 36I engages a corresponding annular protrusion 280 (FIGS. 3, 10) of anvil assembly 30.

The anvil retainer 36A is configured and dimensioned for operative connection to the drive screw 32 (FIG. 6) via a connector 38. The connector 38 includes a central body 38A with a proximal extension 38B for engagement with the distal end of the drive screw 32, e.g., via positioning within a slot (not shown) formed in the distal end of the drive screw 32 having a corresponding configuration and dimensions, and a distal extension 38C. The proximal extension 38B and the distal end of drive screw 32 each define a transverse throughbore (not shown) for receiving a pin, rivet, screw or the like 39A (FIG. 6) in order to fixedly secure the connector 38 to the distal end of the drive screw 32. The distal extension 38C is dimensioned to be received within the longitudinal slot 36F (FIG. 5) formed in the proximal end 36B of the body 36D of the anvil retainer 36A. The distal extension 38C of the connector 38 includes a pair of spaced throughbores (not shown) which align with the throughbores 36G formed in the anvil retainer 36A, to receive pins, screws, rivets or the like 39B (FIG. 6) to fixedly secure the anvil retainer 36A to the proximal extension 38B of the connector 38. Although the anvil retainer 36A and the connector 38 are disclosed as being attached via pins, screws, rivets or the like 39A, 39B, other known fastening techniques are also envisioned, including but not limited to welding, crimping, and interlocking structure.

Referring again to FIGS. 1-4, during use of the stapling device 10, rotation of the approximation knob 22 (FIGS. 1, 2) causes corresponding rotation of the rotatable sleeve 33 about the proximal end of screw 32, which thereby moves the pin 52 (FIG. 2) through the helical channel 50. Since the sleeve 33 is axially fixed to the stationary handle 18, proximal movement of the pin 52 through the helical channel 50 causes retraction of the screw 32 within the stationary handle 18, and distal movement of the pin 52 through the helical channel 50 causes advancement of the screw 32 within the stationary handle 18. Engagement of the anvil assembly 30 and the anvil retainer 38 (FIG. 1) is such that rotation of the approximation knob 22 effectuates movement of the anvil assembly 30 in relation to the shell assembly 31 to thereby move the head portion 16 (FIG. 1) of the surgical stapling device 10 between the unapproximated (spaced) and approximated positions.

Figure 14:
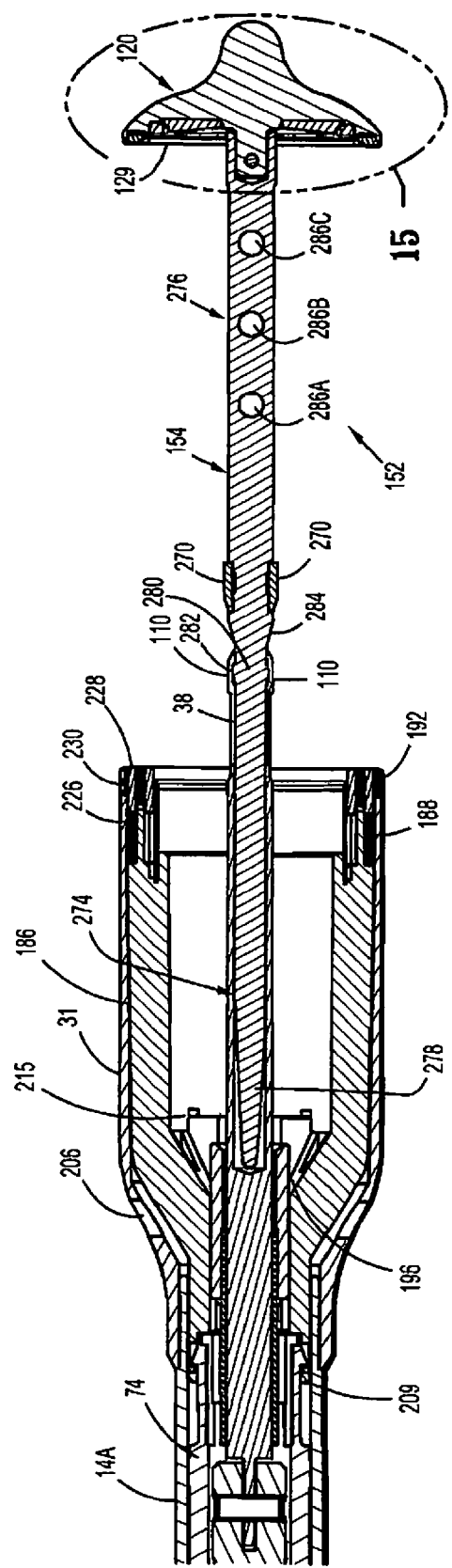
FIG. 14 is an enlarged view of the area of detail indicated in FIG. 13 illustrating a distal portion of the surgical stapling device in the un-approximated position.

With particular reference to FIGS. 1 and 2, the stapling device 10 further includes a firing mechanism to facilitate the ejection of fasteners, e.g., staples 230 (FIG. 14). Specifically, the firing mechanism includes the aforementioned firing trigger 20, a firing link 72, and an elongated pusher link 74 (see also FIG. 4). The trigger 20 includes a body portion 76 (FIG. 2), and a trigger cover 80. The body portion 76 of the trigger 20 is pivotally connected to a coupling member 86 (FIG. 2) that is secured to the proximal end of the pusher link 74 by a pivot pin 84. In an alternative embodiment of the disclosure, however, it is envisioned that the coupling member 86 may be fixedly attached to, e.g., integrally formed with, the pusher link 74.

The firing link 72 has a first end that is pivotally secured to the body portion 76 of the trigger 20, e.g., via a pivot member 87, and a second end that is pivotally secured within a vertical slot 82 (FIGS. 2, 25) that is formed between the stationary handle sections 19A, 19B of the stationary handle 18, e.g., via a pivot member 79. The pivot member 79 is configured and dimensioned for vertical movement within the slot 82, and is biased downwardly towards the bottom of the slot 82 by a spring 82A that is supported within the stationary handle 18.

The body portion 76 of the trigger 20 further includes a pair of abutments 89, 91 (FIG. 2) that are positioned to engage an end 26A of the trigger lock 26 to prevent actuation of trigger 20 prior to approximation of device 10.

The coupling member 86 (FIGS. 2, 4), which is positioned at the proximal end of the elongated pusher link 74, includes a flange 104. A spring 106 is positioned between an inner wall, or abutment, within the stationary handle 18 and flange 104 to thereby bias the pusher link 74 proximally to a retracted, non-fired position. The coupling member 86 includes a pair of wings 108 extending radially outward therefrom for sliding engagement with a channel 111 (FIG. 2) that is formed along the internal walls of the stationary handle 18. Engagement of the wings 108 with the channel 111 maintains proper alignment of the pusher link 74 within the stationary handle 18 during firing of the stapling device 10.

The pusher link 74 is positioned within the outer tube 14a of the body portion 14, and includes structure that is configured and dimensioned to facilitate secure engagement with a pusher back 186 (FIG. 4). The pusher back 186 forms part of shell assembly 31 (FIG. 1), and will be discussed in greater detail below. In the illustrated embodiment, for example, the pusher link 74 includes a pair of engagement fingers 110 (FIG. 4) at a distal end thereof that are configured and dimensioned for secure engagement with members 220 formed in the proximal end of the pusher back 186, e.g., in interlocking relation. Additionally, the pusher link 74 defines a hollow channel 75 extending therethrough to slidably receive the assembled approximation mechanism.

Figure 13:
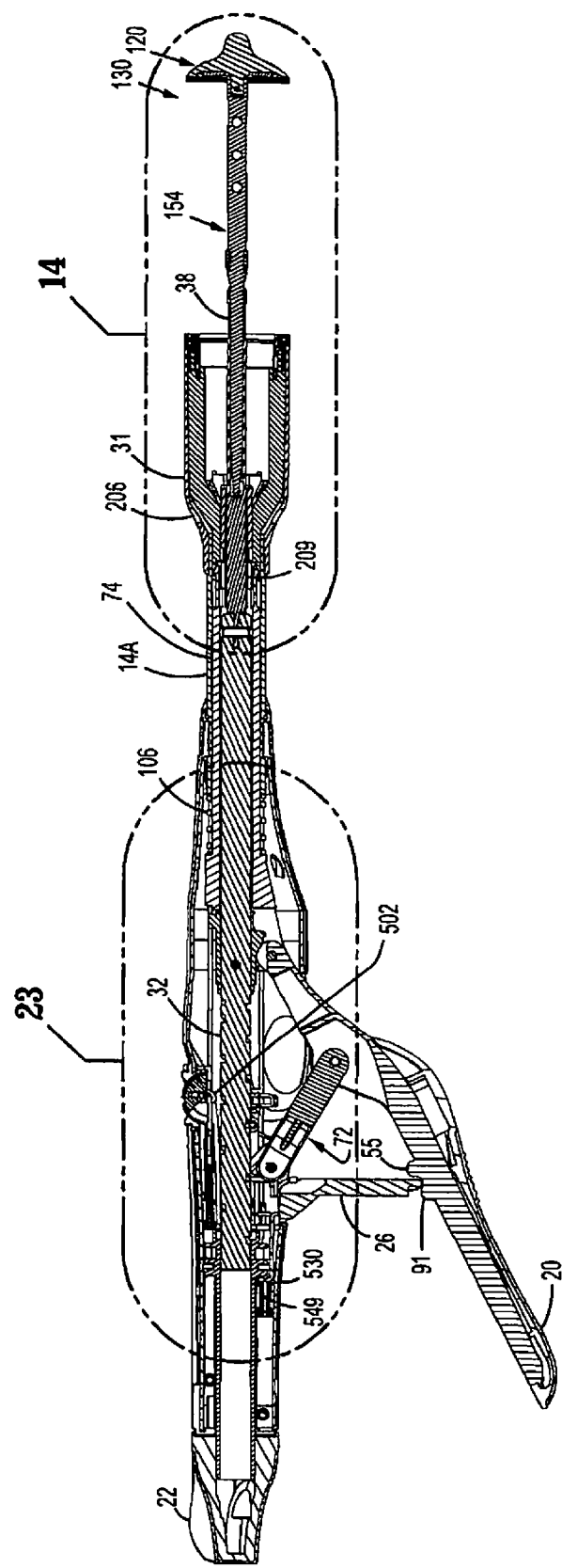
FIG. 13 is a longitudinal cross-sectional view of the surgical stapling device of FIG. 1 with the anvil in the un-approximated position.

Upon actuation of the firing trigger 20, the firing trigger 20 is pivoted about the pivot member 84 which causes the firing link 72 to move proximally until the pivot member 79 engages an abutment surface formed on a screw stop 306 (FIGS. 2, 13,14). The screw stop 306 is connected to the screw 32 in a manner inhibiting relative axial movement between the screw stop 306 and the screw 32 that will be discussed below. Distal movement of the firing trigger 20 causes corresponding distal movement of the pusher link 74 (FIGS. 2, 4) against the bias applied by the spring 106. Since the distal end of the pusher link 74 is connected to the pusher back 186, actuation of the firing trigger 20 effectuates distal advancement of the pusher back 186 within the shell assembly 31 to eject the fasteners 230 from the shell assembly 31.

Referring now to FIGS. 8-15, the anvil assembly 30 will be discussed. The anvil assembly 30 includes an anvil head assembly 120 and an anvil center rod or anvil shaft 152. The anvil head assembly 120 includes a post 122 (FIG. 10), an anvil head 124, a cutting ring 128, and an anvil 129.

The anvil head 124 includes a centrally-positioned bore that receives the post 122, details of which are provided below, as well as vent holes 125 (FIG. 8), a bulbous member 126, and an outer annular recess 136 (FIG. 10) to receive the anvil 129. The bulbous member 126 is configured and dimensioned to allow smooth passage of the anvil assembly 30 through an opening in the patient's tissue, e.g., the patient's anus.

Figure 10:
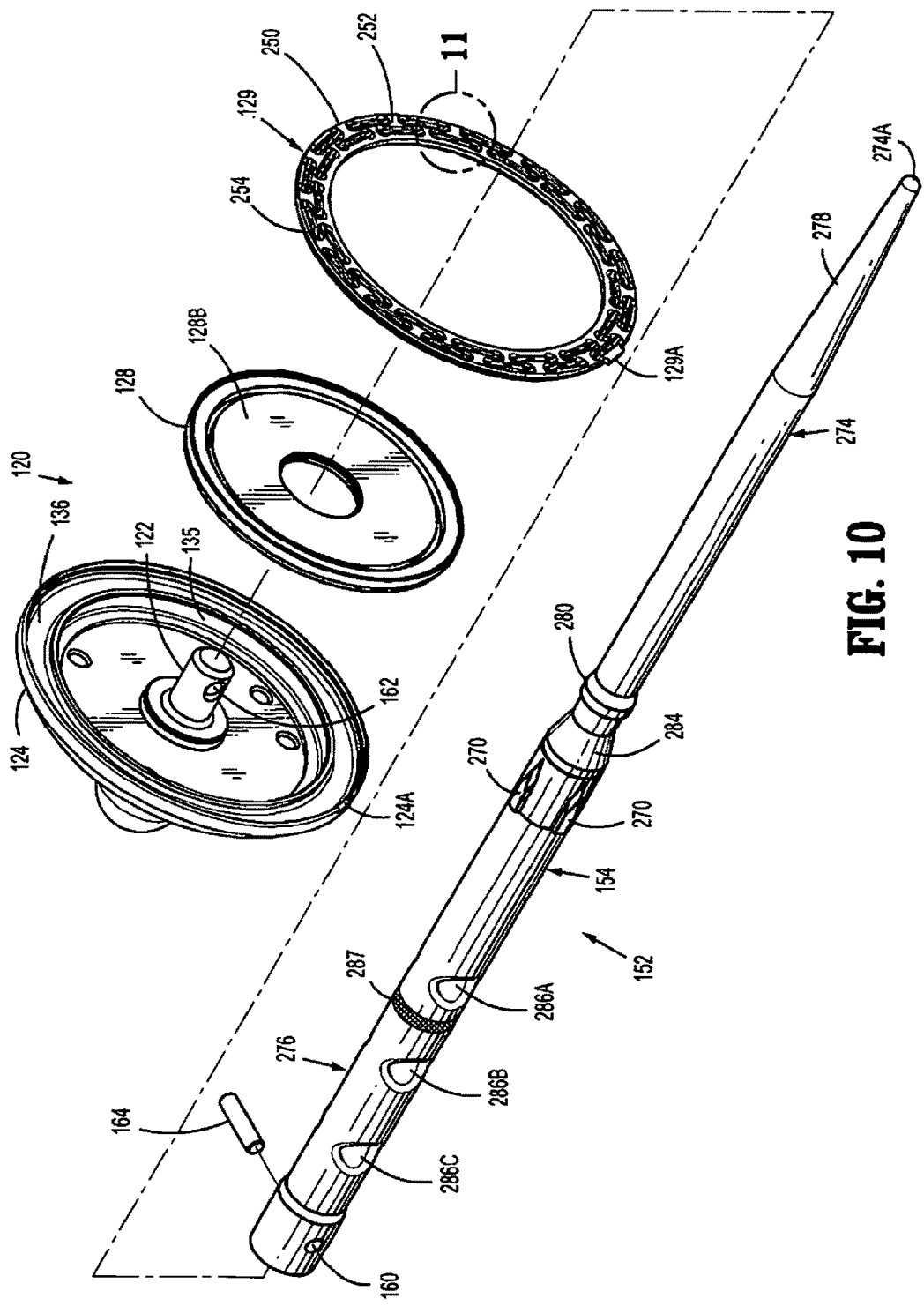
FIG. 10 is a side perspective view of the anvil assembly with parts separated.
Figure 15:
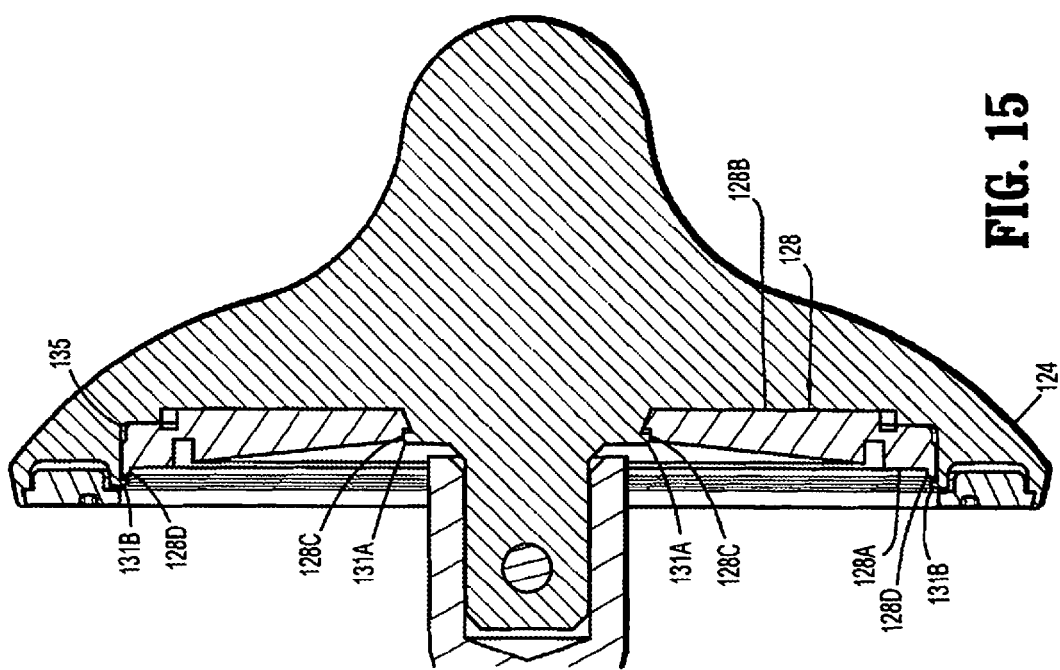
FIG. 15 is an enlarged view of the area of detail indicated in FIG. 14 illustrating the anvil head component of the anvil assembly.

As seen in FIGS. 10 and 15, the cutting ring 128 is an annular member that is positioned within an inner annular recess 135 formed in anvil head 124. The cutting ring 128 includes respective proximal and distal ends 128A, 128B (FIG. 15), and defines an inner proximally facing annular shoulder 128C, as well as an outer proximally facing annular surface 128D. The inner annular shoulder 128C and the annular surface 128D of the cutting ring 128 engage the anvil head 124 such that the cutting ring is retained within the recess 135. For example, as seen in FIG. 15, the anvil head 124 may include an inner wall with an outwardly extending finger 131A that engages the inner annular shoulder 128C, and an outer wall with an inwardly extending finger 131 B that engages the outer annular surface 128D. During use of the stapling device 10, upon firing, the cutting ring 128 is penetrated by the knife 188 (FIG. 4).

Anvil 129 includes structure that is configured and dimensioned for engagement with corresponding structure formed in the anvil head 124 to facilitate proper alignment between the anvil 129 and the outer annular recess 136 formed in the anvil head 124. In the illustrated embodiment, for example, the anvil 129 includes a tab 129A (FIG. 12B) extending radially outwardly therefrom for engagement with a cutout 124A formed in the anvil head 124. It should be appreciated, however, that alternative structure may be employed to achieve proper alignment between the anvil 129 and the anvil head 124.

The anvil 29 is a die-cast member that can be formed from any suitable material. Examples of materials suitable for the construction of the anvil 129, as well as the anvil head 124, include, but are not limited to steel, titanium, magnesium, aluminum, or zinc alloy. It is envisioned that the anvil 129 and the anvil head 124 may be comprised of the same material, or alternatively, that the materials comprising the anvil 129 and the anvil head 124 may be different. In one specific embodiment of the anvil assembly 30, the anvil 129 is formed from the zinc alloy Zamak #3, which includes at least 95% zinc, aluminum, magnesium, and copper.

Figure 11:
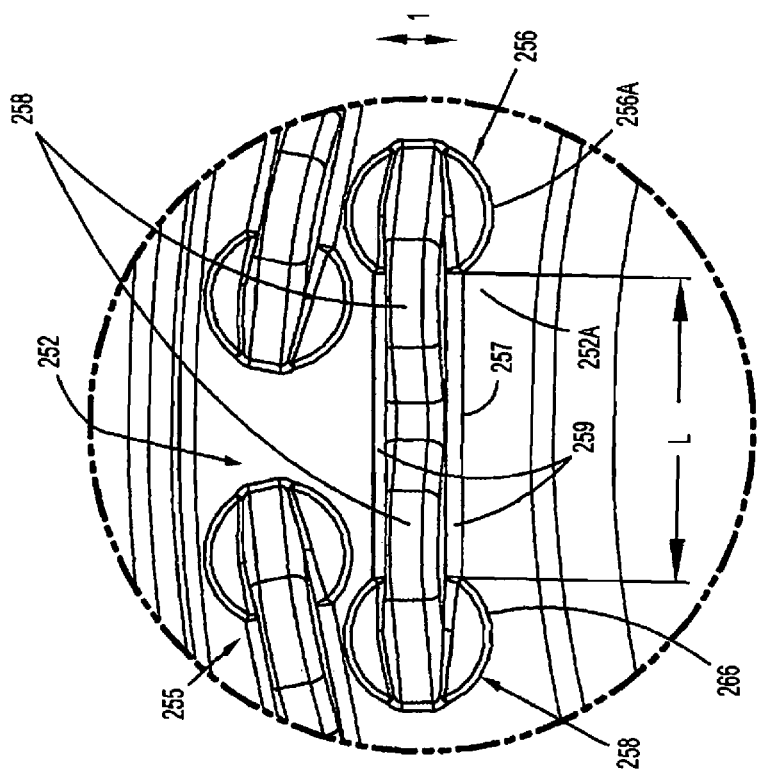
FIG. 11 is an enlarged view of the area of detail indicated in FIG. 10 illustrating a tissue contacting surface of the anvil assembly.

The anvil 129 includes a body 250 with a tissue contacting surface 252, and a bottom surface 254. In one embodiment of the anvil 129, the tissue contacting surface 252 may include a coating 252A, as shown in FIG. 11, that is formed from a suitable biocompatible material. Incorporation of the coating 252A may reduce the likelihood that the patient's tissue will stick, or adhere, to the anvil 129, and/or may enable the anvil 129 to be formed from materials that could not otherwise be included in the construction thereof due to bio-incompatibility, e.g., the aforementioned zinc alloy Zamak #3. In one particular embodiment of the anvil 129, the coating 252A may include Teflon, although the use of other materials is contemplated.

As seen in FIG. 11, the tissue contacting surface 252 of the anvil 129 includes a plurality of pockets 255 that are arranged into a plurality of annular rows to receive and deform corresponding annular rows of staples. In the embodiment of the anvil 129 illustrated in FIGS. 10 and 11, for example, the anvil 129 includes two annular rows of pockets 255. It should be appreciated, however, that the rows of pockets 255 may be present in either greater or fewer numbers in alternative embodiments of the anvil 129.

The pockets 255 include a pair of cavities 256 that are connected by a linear section 257 including a pair of forming surfaces 258. The cavities 256 define an outer rim 256A, and slope inwardly therefrom, i.e., away from the tissue contacting surface 252. The cavities 256 are configured and dimensioned to urge the legs of the fasteners 230 into the linear section 257, and more specifically, into contact with the forming surfaces 258. The presence of the cavities 256 relaxes the tolerances of the stapling device 10 by reducing the precision with which the fasteners 230 need to be ejected from the shell assembly 31 (FIG. 1) in order to facilitate desired contact between the legs of the fasteners 230 and the forming surfaces 258. By reducing such tolerances, the likelihood that an ejected fastener 230 will contact the forming surfaces 258 as desired for staple formation is increased, thereby decreasing the costs associated with manufacture of the device.

In one embodiment of the anvil 129, it is envisioned that the cavities 256 may be substantially spherical in configuration, as best shown in FIG. 11, although alternative configurations are not beyond the scope of the present disclosure. The substantially spherical configuration increases the surface area of the cavities 256 available for contact with the legs of the fasteners 230.

As mentioned above, the cavities 256 are connected by the linear section 257. More specifically, at least a portion of the outer rim 256A of each cavity 256 intersects the linear section 257, e.g., to substantially limit any interruption in the movement of the legs of the surgical fastener 230 from the cavities 256 into contact with the forming surfaces 258. The linear section 257 defines a length "L" that is determined based upon the specific dimensions of the fasteners 230 to be formed. Accordingly, the length "L" of the linear section 257 can be varied in alternative embodiments of the anvil 129 dependent upon the particular configuration and dimensions of the fasteners 230 loaded into the shell assembly 31.

The forming surfaces 258 are arcuate in configuration along the length "L" of the linear section 257, initially curving away from, and then towards, the tissue contacting surface 252. This curvature promotes redirection and deformation of the legs of the fasteners 230 such that the fasteners 230 can achieve a desired formed configuration. In the embodiment of the anvil 129 seen in FIGS. 10 and 11, for example, the forming surfaces 258 are positioned, configured, and dimensioned such that the fasteners 230 achieve a standard "B-shaped" configuration. In alternative embodiments of the anvil 129, however, the position, configuration, and/or dimensions of the forming surfaces 258 can be adjusted to alter the formed configuration of the fasteners 230, e.g., the forming surfaces 258 may be positioned, configured, and dimensioned such that the fasteners 230 achieve a single loop configuration upon formation.

The fastener pockets 255 further include a pair of side walls 259 that extend from the forming surfaces 258 to the tissue contacting surface 252. The side walls 259 are configured and dimensioned to further ensure proper formation of the surgical fasteners 230. For example, it is envisioned that the side walls 259 may define a substantially planar configuration that limits lateral movement of the legs of the surgical fasteners 230 within the fastener pockets 255, i.e., in the direction indicated by arrow 1. Restricting such movement maintains contact between the legs of the fasteners 230 and the forming surfaces 258 until formation of the fasteners 230 is complete.

Figure 12:
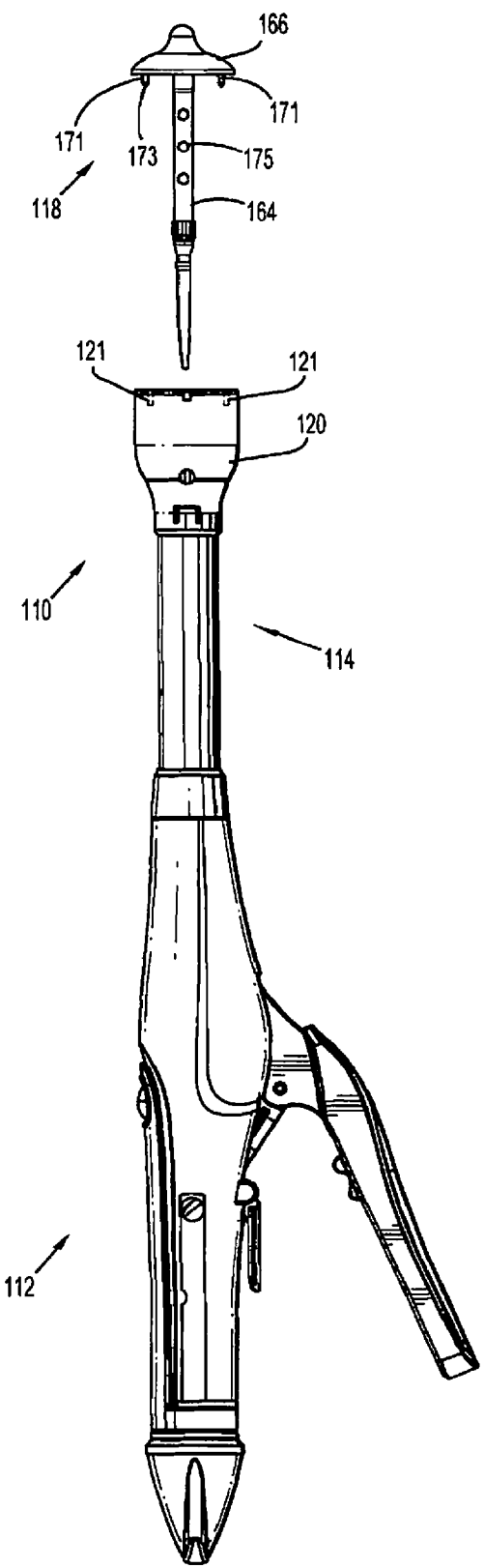
FIG. 12 is a side view of an alternative embodiment of the instrument of the present disclosure having an anvil assembly with alignment pins.
Figure 12A:
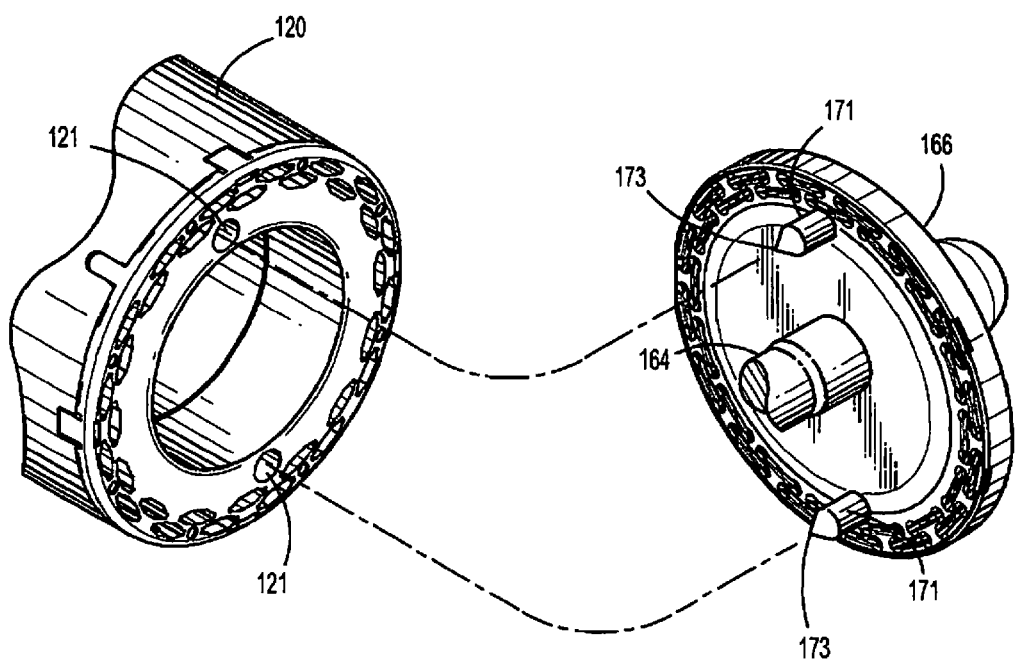
FIG. 12A is a perspective view illustrating the pins of anvil assembly of FIG. 12 and the shell assembly with openings to receive the pins.
Figure 12B:
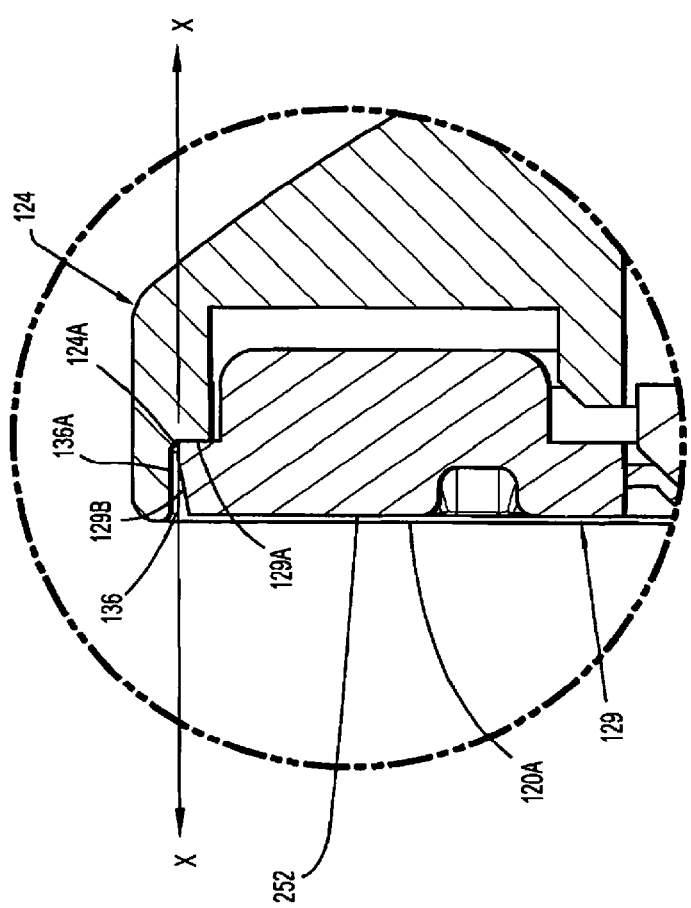
FIGS. 12B and 12C are partial, longitudinal cross-sectional views of the anvil assembly respectively illustrating the anvil assembly before and after deformation to secure the anvil within the anvil head.
Figure 12C:
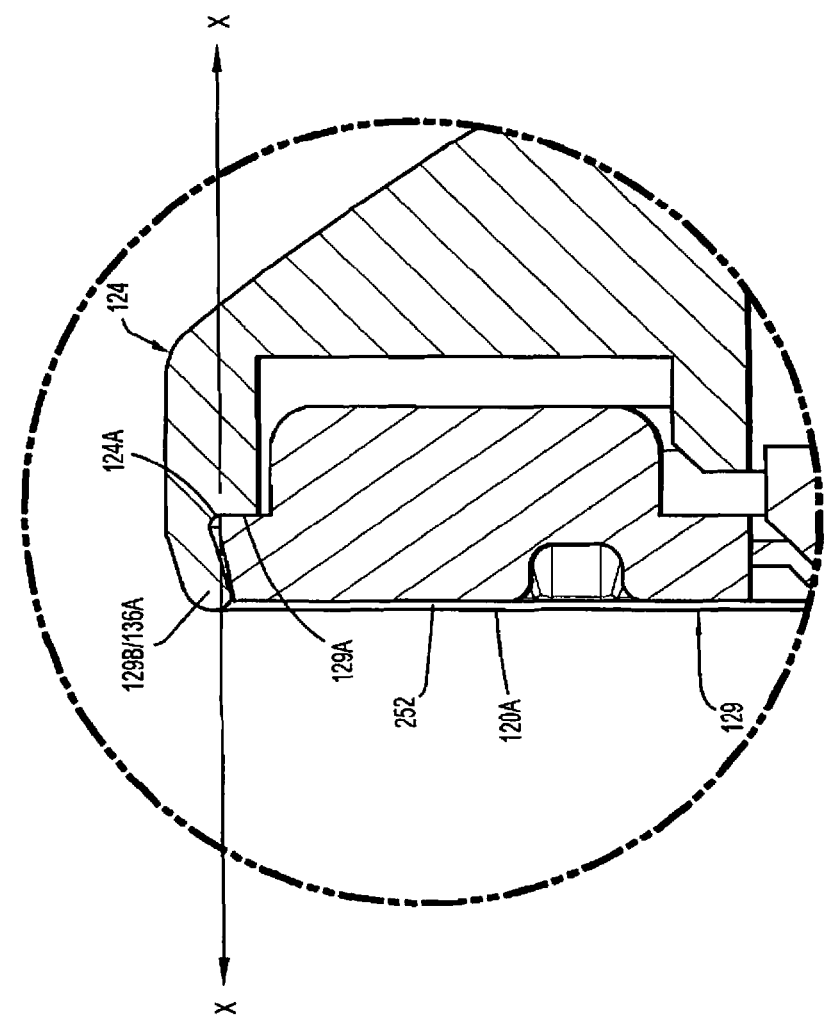

As seen in FIGS. 12B and 12C, the anvil 129 further includes an outer step 129A, and a side wall 129B that is angled towards a longitudinal axis X-X of the anvil assembly 30 (see also FIG. 9). During assembly, the anvil 129 is positioned within the outer annular recess 136 (see also FIG. 10) formed in the anvil head 124 such that the outer step 129A contacts an annular shoulder 124A defined by the anvil head 124. Thereafter, the anvil head 124 is deformed inwardly, e.g., by swaging, towards the longitudinal axis X-X such that an inner surface 136A of the outer annular recess 136 comes into contact with the side wall 129B of the anvil 129, as can be seen in the transition between FIGS. 12B and 12C. After deformation, the anvil head 124 is positioned flush with the tissue contacting surface 252 of the anvil 129 such that the anvil assembly 30 (FIG. 1) defines a proximal-most surface 120A (FIGS. 12B, 12C) that is substantially uniform and substantially planar in configuration.

With particular reference to FIGS. 8-10, 13, and 14, the anvil center rod assembly 152 will be discussed. The anvil center rod assembly 152 includes an anvil center rod 154 having a length sufficient to allow the anvil center rod 154 to protrude from an external surface of the patient's tissue, e.g., from the patient's anus, when properly positioned during a surgical hemorrhoid procedure. For example, for hemorrhoid surgery use, the anvil center rod 154 may have a length of about 13.5 cm (approximately 5.3 inches), although longer and shorter center rods 154 are not beyond the scope of the present disclosure. Allowing the anvil center rod 154 to protrude from the patient's anus allows for improved visibility of the interface between the anvil center rod 154 and the anvil retainer 38.

The anvil center rod 154 includes a proximal portion 274 (FIG. 10) with a tapered blunt end 274A, a distal portion 276, and a central portion 284 that is positioned therebetween. A distal end of the center rod 154 includes a transverse throughbore 160 extending through the central longitudinal axis of the center rod 154 that is positioned for alignment with a transverse throughbore 162 formed in the post 122 of the anvil head assembly 120. An attachment member 164, such as a pin, screw, rivet, or the like, is positioned within the throughbores 160, 162 to secure the post 122 to the center rod 154.

The proximal portion 274 of the center rod 154 includes a trocar 278 with a tapered proximal end. Annular protrusion 280, which is configured and dimensioned for releasable engagement with a corresponding annular recess 282 (FIG. 14) formed at the distal end of the anvil retainer 38. The annular protrusion 280 defines an outer transverse dimension that is greater than the inner transverse dimension of the anvil retainer 38. Accordingly, during attachment of the anvil center rod assembly 152 to the anvil retainer 38 (FIG. 14), proximal advancement of the center rod 154 through the anvil retainer 38 causes engagement between the flexible fingers 272 (FIG. 3) of the anvil retainer 38 and the annular protrusion 280. This engagement forces the flexible fingers 272 radially outward, and thereby facilitates engagement of the annular protrusion 280 and the annular recess 282 (FIG. 14). Engagement between the annular protrusion 280 and the annular recess 282 inhibits relative longitudinal movement between the center rod 154 and the anvil retainer 38 until the application of a predetermined force to the anvil assembly 30 in a distal direction when disconnection of the center rod 154 from the anvil retainer 38 is desired.

Referring back to FIGS. 8-10, the central portion 284 of the center rod 154 has an outer transverse dimension that is greater than an inner transverse dimension defined by the anvil retainer 38 in order to limit insertion of the center rod 154 into the anvil retainer 38. That is, engagement of the central portion 284 with the distal end of the anvil retainer 38 prevents continued insertion of the center rod 154 into the anvil retainer 38.

Figure 34:
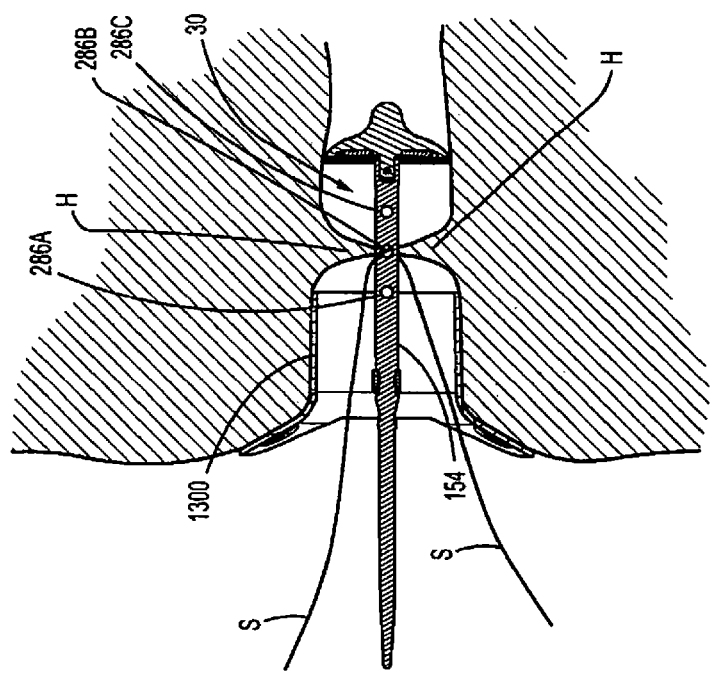
FIG. 34 is a longitudinal cross-sectional view of the port component of the anoscope kit and the anvil assembly component of the surgical stapling device positioned within a patient following purse stringing and illustrating attachment of the purse string suture to the anvil assembly.

The distal portion 276 of the center rod 154 includes one or more apertures, e.g., apertures 286A, 286B, 286C, formed therein that are positioned proximally of the throughbore 160. Although illustrated as including three apertures, it should be appreciated that greater or fewer number of apertures may be included in alternative embodiments of the center rod 154. Although the apertures are show substantially equidistantly spaced, other spacing of the apertures is also contemplated. The apertures 286A-286C extend through the center rod 154, and are configured and dimensioned to receive a flexible member therethrough, such as a length of suture "S" as described below (FIG. 34). In the illustrated embodiment, the apertures 286A-286C are spaced longitudinally along the center rod 154, which allows the clinician to control the amount of tissue drawn into the shell assembly 31. Specifically, by positioning the suture "S" within the proximal-most aperture 286A, a greater amount of tissue will be drawn into the shell assembly 31 when compared to the amount of tissue that will be drawn into the shell assembly 31 by attaching the suture "S" to the distal-most aperture 286C.

In one embodiment of the disclosure, it is contemplated that the center rod 154 may further include a marker such as a ring 287 that is positioned between the apertures 286A and 286B to signify to a clinician that attachment of a suture to the proximal-most aperture will effect a large tissue bite.

The distal portion 276 of the anvil center rod 154 further includes splines 270 which are configured and dimensioned for slidable engagement with corresponding axial grooves (not shown) formed in shell assembly 31 during approximation of the anvil assembly 30 and the shell assembly 31. Engagement between the splines 270 and the axial grooves of the shell assembly 31 acts to properly align the anvil assembly 30 with the shell assembly 31 such that the fastener anvil pockets 255 formed in the tissue contacting surface 252 of the anvil 129 align with the slots 228 (FIG. 4) formed in the fastener guide 192.

Figure 16:
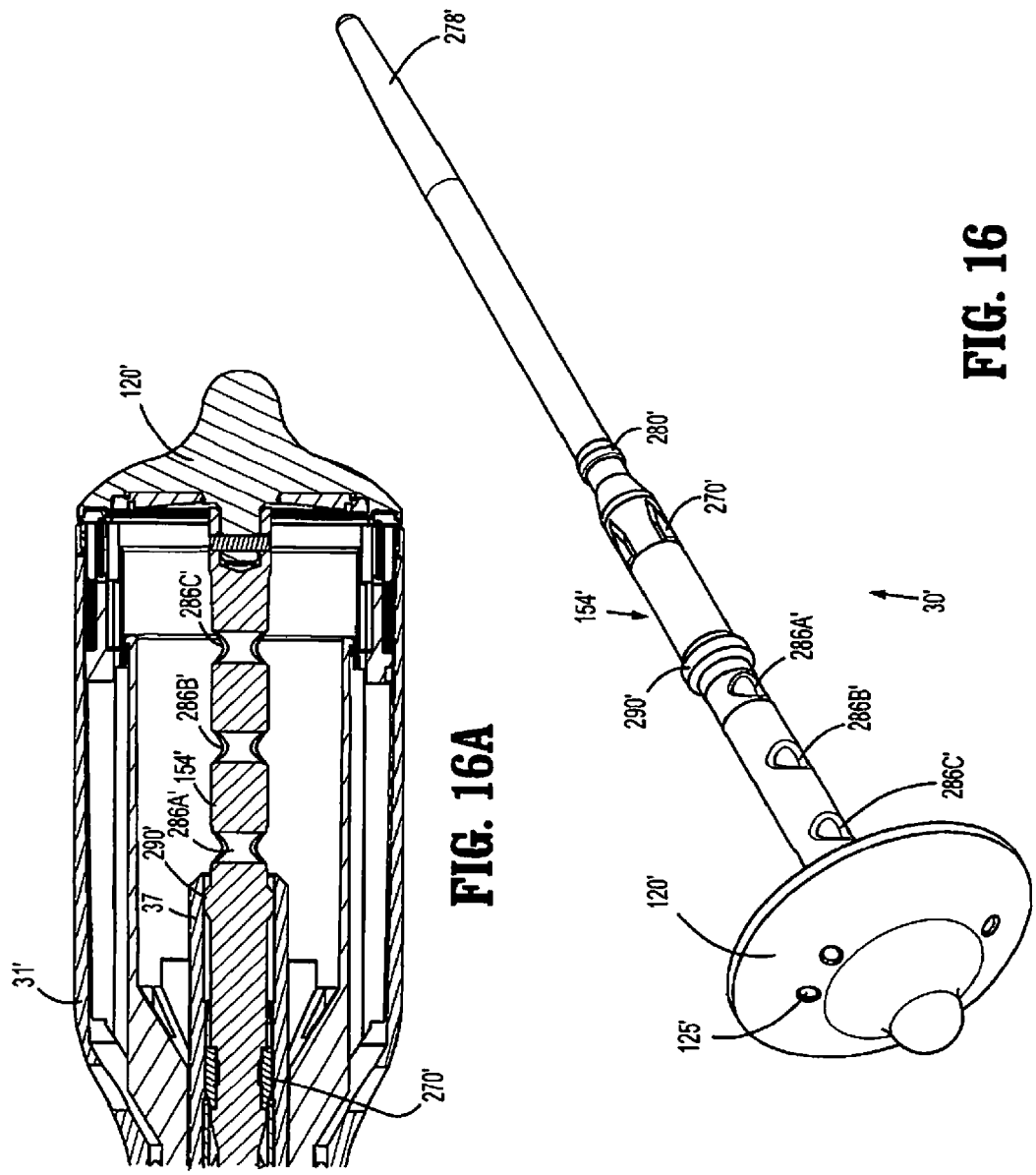
FIG. 16 is a side, perspective view of the anvil assembly according to an alternative embodiment of the present disclosure.

In an alternate embodiment shown in FIGS. 16 and 16A, a center rod (anvil shaft) 154' is disclosed. The center rod 154' is substantially similar to the center rod 154 described herein, and accordingly, will only be discussed in detail with respect to any differences therefrom. Components of the center rod 154' corresponding to the components of center rod 154 are labeled with prime designations. Thus, for example, center rod 154' has apertures 286A', 286B', 286C', is mounted to head assembly 120' and has trocar 278'.

The center rod 154' includes an outer annular member (protrusion) 280' similar to annular protrusion 280 of FIG. 19. To attach the anvil assembly 30' to the anvil retainer 38, the center rod 154' (like center rod 154) is positioned within the anvil retainer 38 (FIGS. 1 and 5), and advanced proximally such that the annular protrusion 280' of the center rod 154' engages the flexible fingers 272 of the anvil retainer 38. Upon engagement of the annular protrusion 280' with the flexible fingers 272, the flexible fingers 272 are forced outwardly, thereby facilitating engagement of the annular protrusion 280' and the annular recess 282 of the anvil retainer 38 to inhibit relative longitudinal movement between the center rod 154' in the same manner as described above with respect to protrusion 280 of FIG. 10.

Center rod 154' includes a second raised annular ring or interference rib 290 configured and dimensioned to enhance frictional engagement of the center rod 154' with the shell assembly 31 (FIG. 1) to further enhance stability. To achieve frictional engagement with the shell assembly 31', the annular member 290' is configured and dimensioned to engage a raised boss 37 of the shell assembly 31' when the anvil assembly 30' is attached to the anvil retainer 38 and approximated. This is illustrated in FIG. 16A where the annular member 290' engages the raised shell boss 37. As shown, the member 290 is positioned proximally of the suture apertures 286A', 286B', 286C, and in the illustrated embodiment is positioned adjacent the proximalmost aperture 286A'. Other locations are also contemplated. Note the shell assembly 31' is substantially identical to shell 31 described herein except for the raised boss 37 which engages annular member 290 when the anvil shaft 154' is attached to the surgical stapling instrument 10. This interference provides an additional engagement to enhance the stability of the anvil assembly when attached to the instrument. Anvil shaft 154' also includes a plurality of machined splines 270' for alignment with grooves of the shell assembly 31' in the same manner as splines 27 described above. Alternatively, the splines can be overmolded on the center rod 154'.

Referring now to FIGS. 1 and 4, the shell assembly 31 will be discussed in detail. The shell assembly 31 includes a shell 182, a pusher back 186, a cylindrical knife 188, and a fastener guide 192. The shell 182 has an outer housing portion 194 defining a throughbore 198, and includes a distal cylindrical section 200, a central conical section 202 and a proximal cylindrical section 204. A plurality of openings 206 are formed in the conical section 202 that are configured and dimensioned to permit the passage of fluid and tissue therethrough during use of the stapling device 10 (FIG. 1). A pair of flexible engagement members 207 are formed on the proximal cylindrical section 204 of the shell 182. As illustrated, the engagement members 207 are positioned in diametrical opposition. However, alternative configurations for the engagement members 207 are also contemplated. The engagement members 207 are positioned within openings 207A formed on the distal end of the outer tube 14A to secure the shell 182 to the elongated body 14. A pair of openings 211 are formed in the proximal end of outer tube 14A, only one of which is shown, that are configured and dimensioned to receive protrusions (not shown) formed on the internal wall of the stationary handle 18 to facilitate attachment of the outer tube 14A to the handle portion 12.

The pusher back 186 is slidably positioned within the shell 182, and includes a throughbore 208A, a distal cylindrical section 210 that is configured and dimensioned for slidable reception by the distal cylindrical section 200 of the shell 182, a central conical section 212, a proximal cylindrical section 214, and a receptacle 215 (FIG. 14) to receive excised tissue. The receptacle 215 is configured to define a depth substantially within the range of approximately 0.275 cm (approximately 0.75 inches) to approximately 0.79 cm (approximately 2.0 inches). For example, in one embodiment, the receptacle 215 is configured to define a depth of approximately 0.52 cm (approximately 1.33 inches).

Referring again to FIG. 4, the cylindrical knife 188 is retained within the throughbore 208A of the pusher back 186 to fixedly the secure knife 188 in relation to the pusher 190. The knife 188 may be retained within the pusher back 186 in any suitable manner, including but not limited to the use of adhesives, crimping, pins, a friction fit, etc.

As mentioned earlier, the pusher back 186 includes the aforementioned members 220, which are configured to securely engage the resilient fingers 110 of the pusher link 74. Engagement of the members 220 and the fingers 110 fastens the pusher link 74 to the pusher back 186 such that a distal face of the pusher link 74 abuts a proximal face of the pusher back 186. At a distal end, the pusher back 186 includes a pusher 190 incorporating a plurality of distally extending fingers 226 that are slidably positioned within the fastener receiving slots 228 formed in the fastener guide 192 to eject the fasteners 230.

Figure 17:
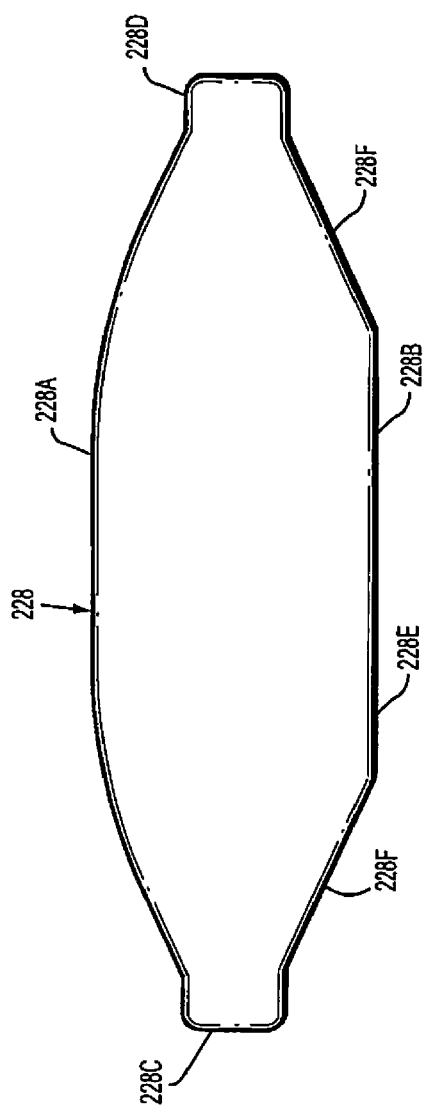
FIG. 17 is a top view of an exemplary slot formed in the shell assembly that is configured and dimensioned to receive a surgical fastener.
Figure 20:
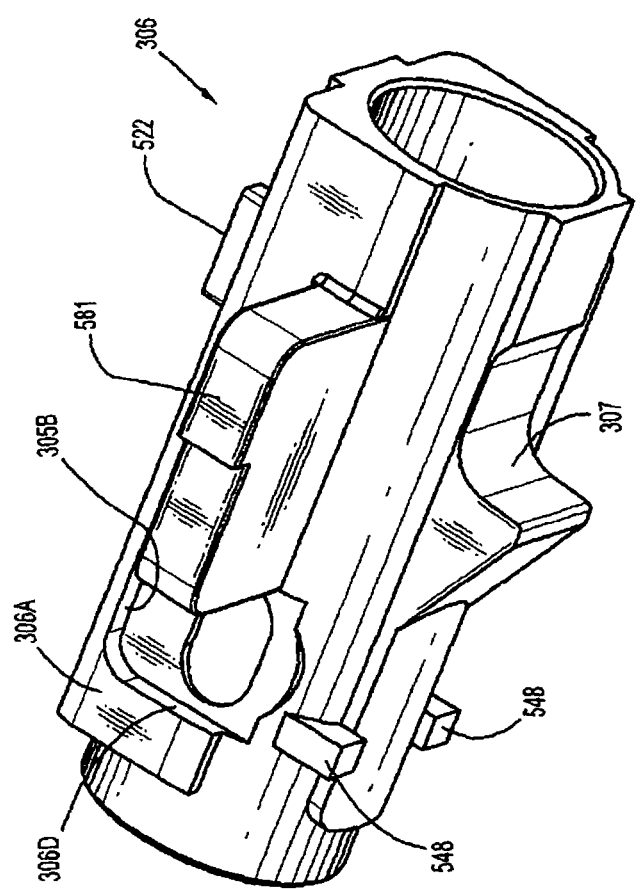
FIG. 20 is a side perspective view of the screw stop shown in FIGS. 18 and 19.

With reference to FIG. 17, the slots 228 (see also FIG. 4) formed in the fastener guide 192 will be described. In one illustrative embodiment, the slots 228 each have a first sidewall 228A, a second sidewall 228B, and a pair of substantially rectangular recesses 228C, 228D that are positioned at opposite ends of the respective first and second sidewalls 228A, 228B. The first sidewall 228A is substantially convex, and includes a first end that is connected to the recess 228C, and a second end that is connected to the recess 228D. The second sidewall 228B includes a sidewall portion 228E with a longitudinal axis that is parallel to the longitudinal axis of the slot 228, and a pair of angled sidewall portions 228F. Each angled sidewall portion 228F interconnects one end of the sidewall portion 228E with one of recesses 228C, 228D. Each of the recess 228C, 228D is configured and dimensioned to frictionally retain a leg of the fasteners 230 (FIG. 14) therein. It should be appreciated that the configuration of the slots 228 may be altered or varied in alternative embodiments of the present disclosure.

Returning now to FIG. 4, during use of the stapling device 10, when the pusher link 74 is advanced distally in response to actuation of the firing trigger 20 (FIG. 1), the pusher back 186 is advanced distally within the shell 182. Advancement of the pusher back 186 causes corresponding advancement of the fingers 226 provided on the pusher 190 through the slots 228 of the fastener guide 192 to advance and eject the fasteners 230 from the fastener guide 192 into the fastener deforming pockets 255 formed in the tissue contacting surface 252 of the anvil 129. Since the knife 188 is secured to the pusher back 186, the knife 188 is also advanced distally to cut tissue positioned between the anvil assembly 30 and the shell assembly 31.

The shell 182 further includes a rigid bushing 209 that is supported in the proximal end of an inner guide portion 196 (FIG. 14). The rigid bushing 209 includes a throughbore 209A extending therethrough to slidably receive the anvil retainer 38 and the center rod of the anvil assembly 30. The bushing 209 provides lateral support for the flexible fingers 272 (FIG. 3) of the anvil retainer 38 upon approximation of the anvil assembly 30 to inhibit disengagement of the anvil assembly 30 from the anvil retainer 38. When the anvil assembly 30 is un-approximated, i.e., spaced apart from the shell assembly 31, the flexible fingers 272 of the anvil retainer 38 are positioned externally of the bushing 209 to permit outward flexure of the flexible fingers 272 to facilitate removal of the anvil assembly 30 from the anvil retainer 38.

With reference to FIGS. 2 and 18-20, a cam adjustment member 400 is secured by a set screw 312 onto a sidewall 306A of the screw stop 306. Specifically, the cam adjustment member 400 is positioned within a recess 306B formed in the sidewall 306A. The cam adjustment member 400 includes a circular disc 402 having a throughbore 404 that is eccentrically formed through the disc 402, and dimensioned to receive the set screw 312. A smaller notch, or hole 406 is also formed in the disc 402, and is dimensioned to receive a tip of an adjustment tool (not shown). The recess 306B includes a forward abutment surface 306C and a rear abutment surface 306D, and is dimensioned to receive the disc 402 such that the outer edge of the disc 402 abuts the respective forward and rear abutment surfaces 306C, 306D. The set screw 312 extends through the disc 402 and the screw stop 306 upon assembly.

The cam adjustment member 400 allows for the axial position of the screw stop 306 on the screw 32 to be adjusted, and thus, for adjustment of the air gap defined between the shell assembly 31 and the anvil assembly 30 during manufacture. More specifically, loosening of the set screw 312 allows the disc 402 to rotate within the recess 306B of the screw stop 306 while still remaining fixed to the screw 32. Since the disc 402 is eccentrically mounted about the set screw 312, and is in engagement with the respective forward and rear abutment surfaces 306C, 306D of the recess 306B, rotation of the disc 402 about the fixed set screw 312 urges the screw stop 306 axially along the screw 32 to adjust the axial position of the screw stop 306 on the screw 32. For example, when the disc 402 is rotated clockwise, i.e., in the direction identified by arrow "B" in FIG. 19, the screw stop 306 will be moved axially in relation to the screw 32 in the direction indicated by arrow "C" in response to engagement between the outer edge of the disc 402 and the rear abutment surface 306D of the recess 306B. Conversely, when the disc 402 is rotated counter-clockwise, i.e., in the direction indicated by arrow "D" in FIG. 18, the screw stop 306 will be moved axially in relation to the screw 32 in the direction indicated by arrow "E" in response to engagement between the outer edge of the disc 402 and the forward abutment surface 306C of the recess 306B.

Figure 21A:
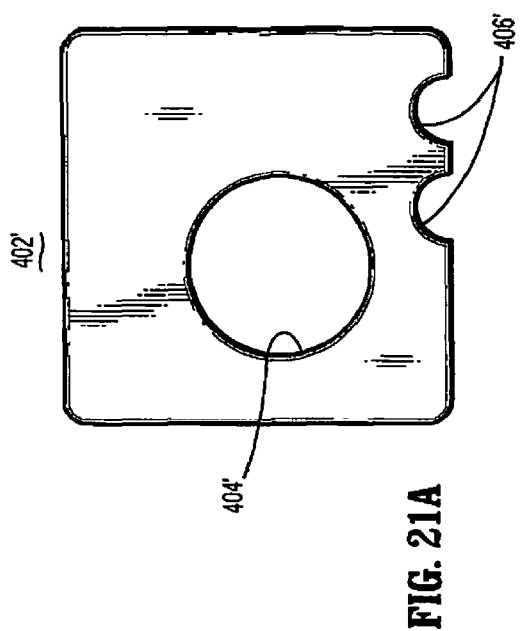
FIGS. 21A and 21B are side views illustrating washers for use with the screw stop shown in FIGS. 18 and 19.
Figure 21B:
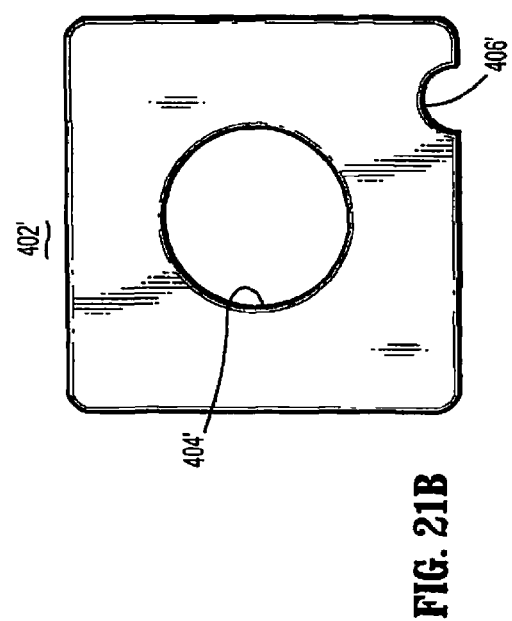
Figure 22:
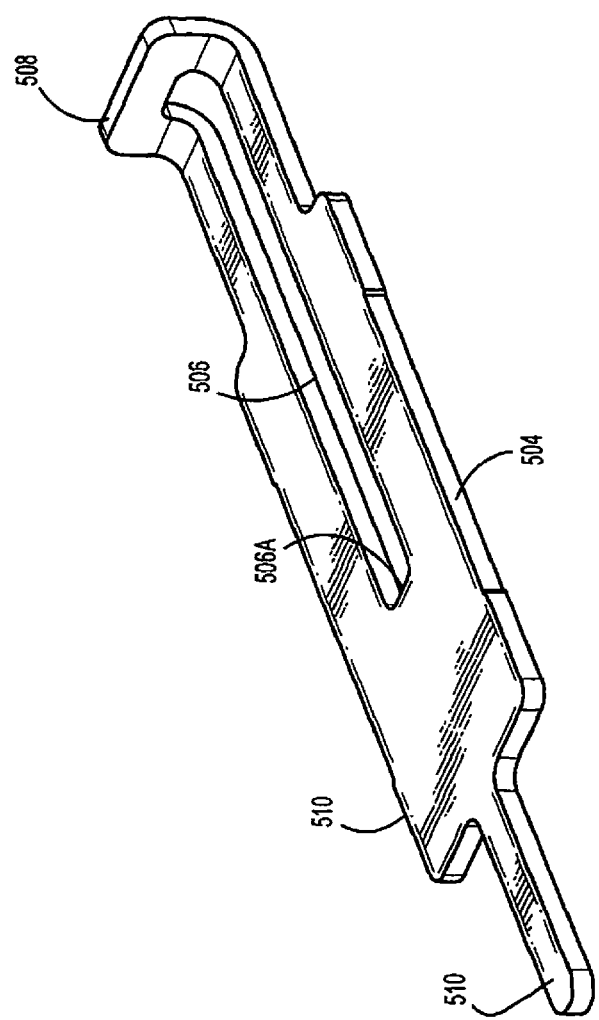
FIG. 22 is a side, perspective view of a slide member component of an indicator mechanism of the surgical stapling device.

In an alternative embodiment, the circular disc 402 may be replaced with the rectangular member 402' shown in FIG. 21A or 21B, which presets the size of the air gap defined between the shell assembly 31 and the anvil assembly 30, and does not provide for adjustment of the screw stop 306 on the screw 32. The rectangular member 402' includes an opening 404' that is configured and dimensioned to receive the set screw 302 of FIG. 2 to properly locate the screw stop 306 on the screw 32. The position of the opening 404' on the rectangular member 402' is selected to provide the appropriate size air gap for a particular size fastener, and will vary depending on the particular size fastener, e.g., 3.5 mm or 4.8 mm fasteners, that is housed in the shell assembly 31. The rectangular member 402' includes one or more notches 406' to identify during manufacture the appropriate rectangular member 404' to use for the size fasteners loaded in the stapling device to ensure setting of the appropriate size air gap.

With reference now to FIGS. 1, 2, 22, and 23, the stapling device 10 may further incorporate an indicator mechanism that provides the clinician with an indication that the stapling device 10 has not been approximated, and is not in a fire-ready condition. The indicator mechanism includes the aforementioned indicator 24, as well as a lens cover 24A, and a slide member 500. The indicator is described in detail in U.S. Pat. No. 7,303,106, the entire contents of which are incorporated herein by reference.

The indicator 24 includes indicia providing the clinician with information regarding whether or not the stapling device 10 is read to fire, and is pivotally supported about a pivot member 502. It is envisioned that the pivot member 502 may be formed monolithically with the handle sections 19A, 19B of the stapling device 10. The lens cover 24a is positioned above the indicator 24, and may be include magnification material to facilitate visualization of the indicator 24.

The slide member 500 of the indicator mechanism includes a body portion 504 having an elongated slot 506 formed therein, a distal abutment member or upturned lip portion 508, and a proximal extension 510. The slide member 500 is slidably positioned between the handle sections 19A, 19B of the device 10, and the proximal extension 510 is slidably supported within the stationary handle 18 by support structure 516. A biasing member 512, e.g., a coil spring, is positioned in compression about the proximal extension 510 between the support structure 516 and the body portion 504 of the slide member 500 to urge the slide member 500 distally within the stationary handle 18.

The indicator 24 includes a pair of downwardly extending projections 518, 520 that are positioned about the pivot member 502. The upturned lip portion 508 of slide member 500 is positioned between the projections 518, 520, and is positioned to engage the projections 518, 520 as the slide member 500 moves within the stationary handle 18. When the stapling device 10 is in an unfired position, the biasing member 512 urges the slide member 500 distally to move the lip portion 508 into engagement with the projection 518 to pivot the indicator 24 to a first position, which identifies that the stapling device 10 is not in a fire-ready condition.

Figure 23:
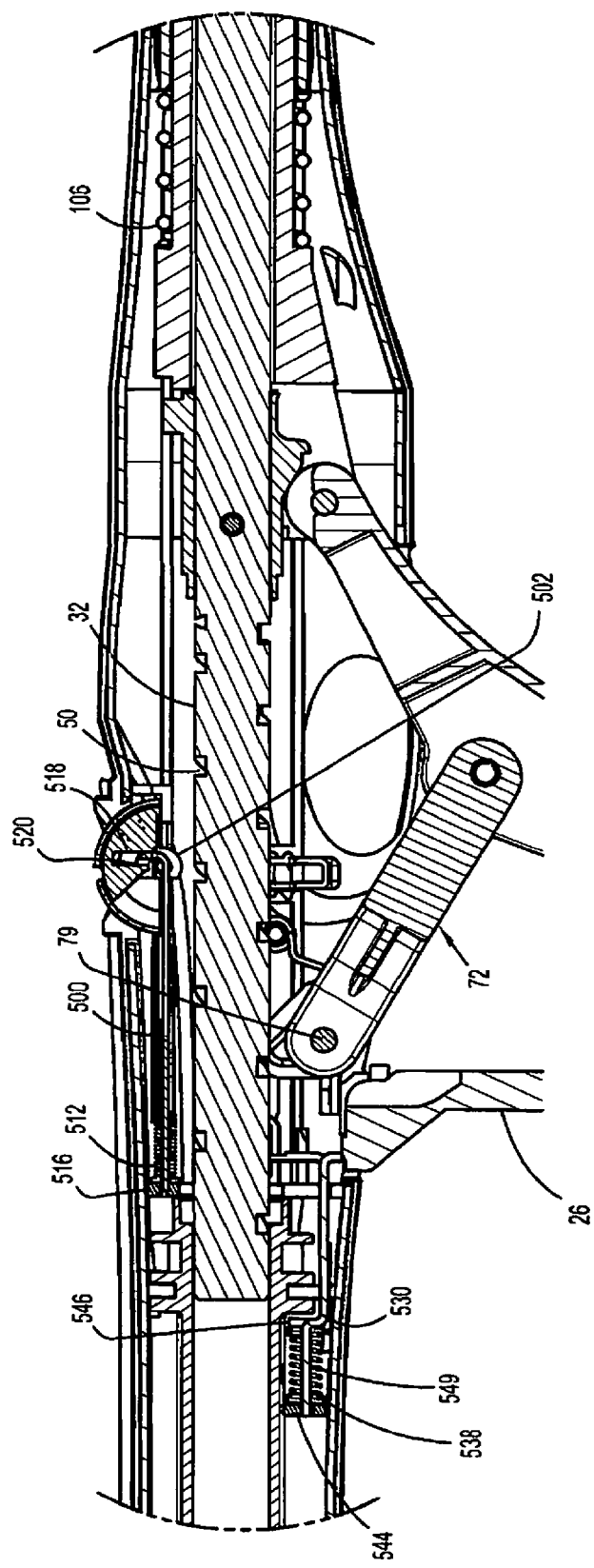
FIG. 23 is an enlarged view of the area of detail indicated in FIG. 13 illustrating the indicator mechanism and drive screw in the unapproximated position.

As discussed above, the screw stop 306 is fixedly attached to the screw 32. The screw stop 306 includes a first engagement member 522 (FIG. 2) that is positioned to travel through the slot 506 formed in slide member 500 (FIG. 22) and engage the proximal end 506A of the slot 506 during approximation of the stapling device 10. When the engagement member 522 abuts the proximal end 506A of the slot 506, further approximation of the stapling device 10 moves the slide member 500 proximally within the stationary handle 18 against the bias of the spring 512 such that the upturned lip 508 of the slide member 500 engages the projections 518, 520 of the indicator 24, as shown in FIG. 23. Engagement between the projections 518, 520 and the lip 508 causes the indicator 24 to pivot about the pivot member 502 to a second position, in which the indicator 24 provides the clinician with an indication that the stapling device 10 has been sufficiently approximated, and is ready for firing.

Figure 25:
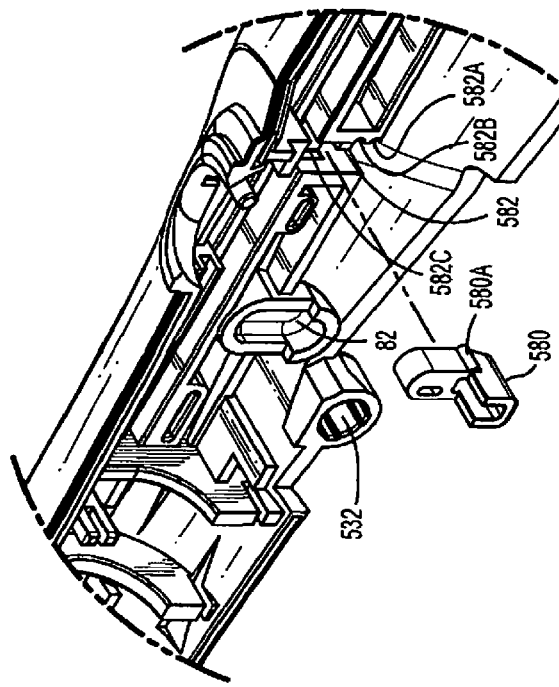
FIG. 25 is an enlarged view of the area of detail indicated in FIG. 2 illustrating an abutment member component of a tactile indicator mechanism.
Figure 24:
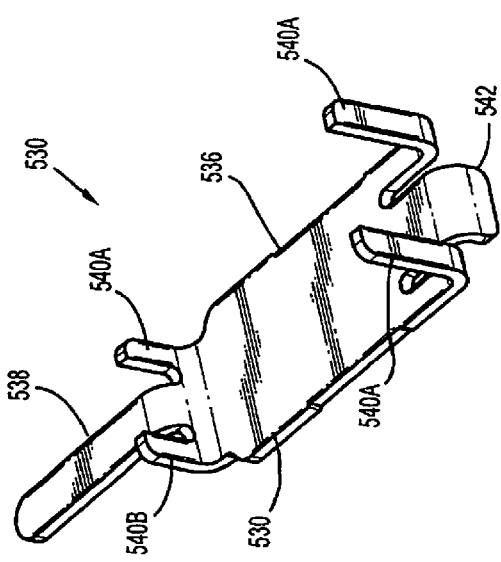
FIG. 24 is a top, perspective view of a lockout member for use with the surgical stapling device to prevent inadvertent firing.

Referring now to FIGS. 2, 24 and 25, the firing-lockout mechanism will be discussed. The firing lockout mechanism includes the aforementioned trigger lock 26, as well as a lockout member 530. The trigger lock 26 is pivotally supported within bores 532 formed in the handle sections 19A, 19B (FIG. 2), e.g., about a pivot member 534. The pivot member 534 extends from an upper edge of the trigger lock 26, and is T-shaped such that the pivot member 534 frictionally engages an inner wall of the bores 532 to prevent free rotation of the trigger lock 26. The trigger lock 26 is positioned between abutments 89, 91 formed on the firing trigger 20 to prevent actuation of the trigger 20 when the trigger lock 26 is in a locked position.

The lockout member 530 (FIG. 24) includes a body portion 536, a proximal extension 538, a pair of front legs 540A, a pair of rear legs 540B, and an abutment member or downturned lip portion 542. The lockout member 530 is slidably positioned between respective first and second stops 544 and 546 (FIG. 23) formed on an internal wall of the handle sections 19A, 19B (FIG. 2). The stop 544 is configured, dimensioned, and positioned to engage the extension 538 of the lockout member 530, and the front legs 540A of the lockout member 530. A biasing member 549 is positioned between the stop 544 and the rear legs 540B about the proximal extension 538 to urge the lockout 530 to a distal-most position wherein the legs 540A abut the stop 546. In this position, the extension 26B (FIG. 2) of the trigger lock 26 is positioned beneath the lip portion 542 of the lockout member 530 to prevent pivotal movement of the trigger lock 26, thus preventing actuation of the stapling device 10.

During use, when the anvil assembly 30 and the shell assembly 31 are approximated, the screw 32 (FIG. 2) is moved proximally within the stationary handle 18, and one or more engagement members 548 formed on the screw stop 306 abut the front legs 540A of the lockout member 530 to move the lockout member 530 proximally against the bias of the member 549 to a position in which the lip portion 542 is spaced proximally from the extension 26b of the trigger lock 26. In this position of the lockout member 530, the trigger lock 526 can be pivoted to a position that does not obstruct operation of the trigger 20 such that the stapling device 10 can be fired.

Figure 26:
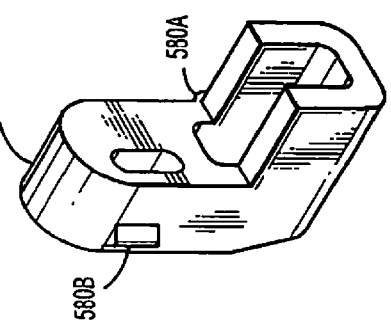
FIG. 26 is a side, perspective view of the abutment member illustrated in FIG. 25.

With reference to FIGS. 25 and 26, the stapling device 10 may further include a tactile indicator mechanism. The tactile indicator mechanism is provided in stationary handle 18 (FIG. 1), and includes an abutment member 580 that is slidably positioned in a vertical slot 582 defined within the handle sections 19A, 19B. The abutment member 580 includes a protuberance 580A, and a guide rib 580B. The protuberance 580A is configured and dimensioned to be received within one of two detents 582A, 582B formed along a wall of the slot 582. The abutment member 580 is movable from a retracted (downward) position, wherein the protuberance 580A is positioned within the detent 582A, to an extended (upward) position, wherein the protuberance 580A is positioned within the detent 582B. Engagement between the protuberance 580A and the detent 582A retains the abutment member 580 in the downward position, and engagement between the protuberance 580A and the detent 582B retains the abutment member 580 in the upward position. The vertical slot 582 may further include a detent 582C that is configured, dimensioned, and positioned to slidably receive guide the rib 580B, and thereby maintain the abutment member 580 in contact with the slot 582.

Prior to firing of the stapling device 10, the abutment member 580 is located in the retracted (downward) position. When the stapling device 10 is fired, an extension 590 (FIG. 2) of the firing link 72 engages the abutment member 580, and moves the abutment member 580 from its retracted to its extended position. In the extended position, the abutment member 580 extends into the channel 111 (FIG. 2) of the stationary handle 18.

The screw stop 306 further includes a pair of wings for slidable engagement with the channel 111 (FIG. 2) of the stationary handle 18. After the stapling device 10 has been fired, the abutment member 580 (FIGS. 25, 26) is positioned within the channel 111. During unapproximation of the anvil assembly 30 and the shell assembly 31, after the anvil assembly 30 has been separated from the shell assembly 31 by a distance sufficient to allow the anvil assembly 30 to be removed from the anvil retainer 38, one of the wings 584 of the screw stop 306 engages the abutment member 580. This engagement between the abutment member 580 and the wing 584 of the screw stop 306 provides a tactile and/or an audible indication to the clinician that the anvil assembly 30 can be removed or disengaged from the anvil retainer 38. If the surgical stapling device 10 is un-approximated further, the wings 584 will force abutment member 580 from the extended position back to the retracted position.

Figure 30:
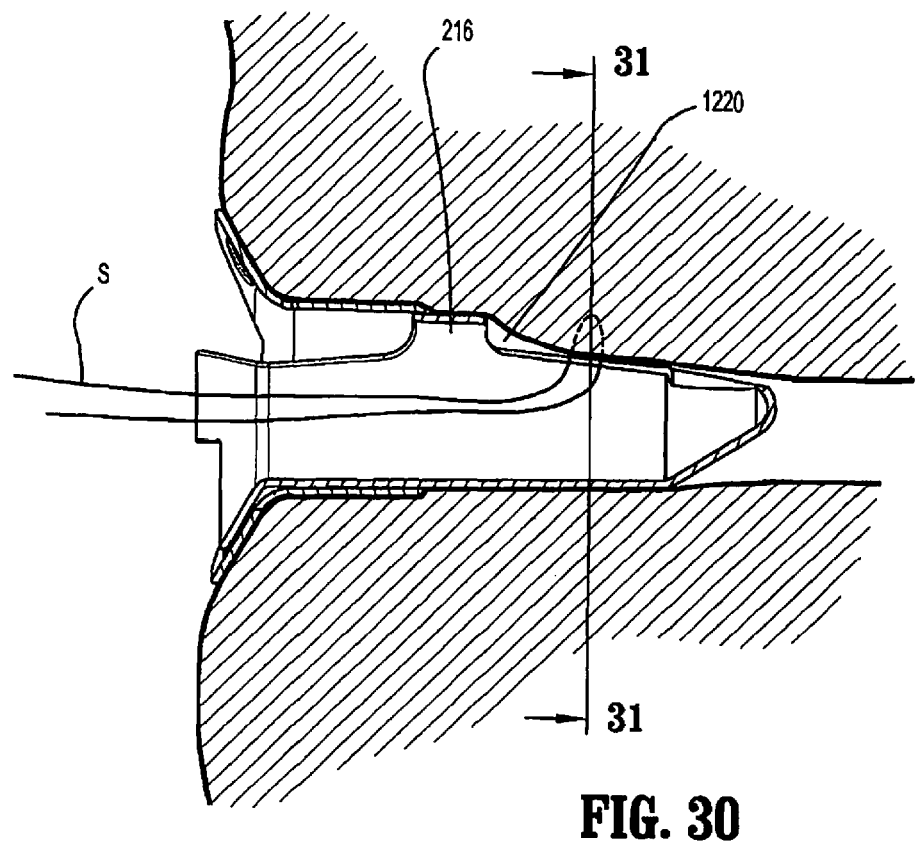
FIG. 30 is a longitudinal cross-sectional view of the anoscope kit positioned within a patient following removal of the obturator and application of a purse string suture.
Figure 35:
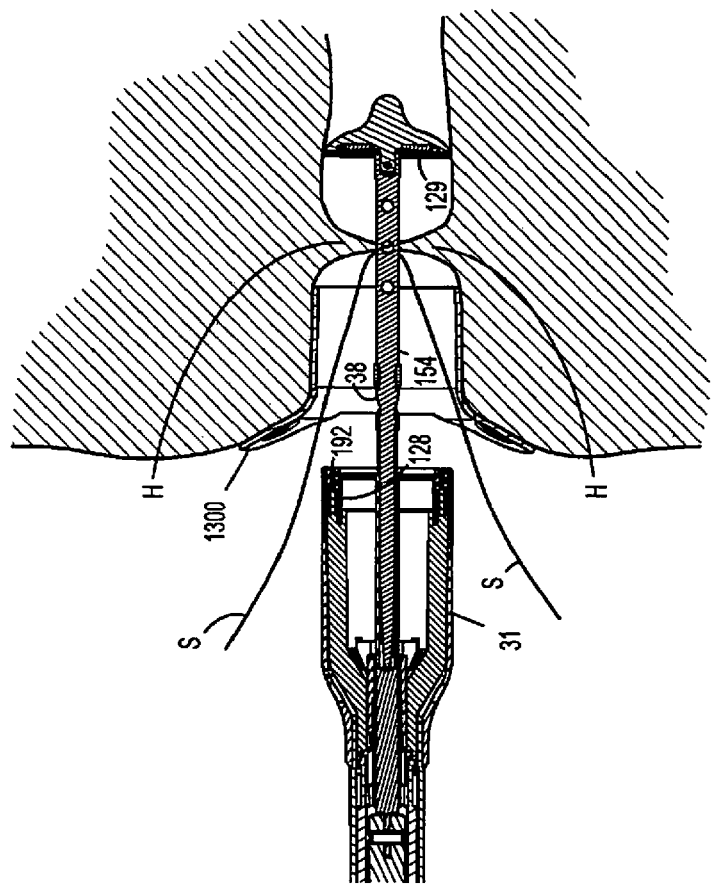
FIG. 35 is a longitudinal cross-sectional view of the port component of the anoscope kit and the anvil assembly component of the surgical stapling device positioned within a patient following purse stringing and attachment of the anvil assembly to the anvil retainer of the surgical stapling instrument.

As discussed above, the stapling device 10 is particularly suitable for use in a surgical hemorrhoid procedure, although it can be used in other procedures. During such a procedure, an access port, such as the access port 1300 shown in FIG. 27, may be inserted into the patient's anus to facilitate access to the target tissue, e.g., prolapsed colon tissue, as seen in FIGS. 30-33. Next, the flexible member, such as the purse string suture "S" seen in FIG. 30, is placed into, above, or in the vicinity of the target tissue, and the anvil assembly 30 is inserted through the access port into the anus and rectum. The bulbous member 126 included on the anvil head 124 allows for smooth passage of the anvil assembly 30 through the body orifice, and past the purse string suture S. Thereafter, the purse string suture is inserted into one of the apertures 286A-286C formed in the center rod 154, as seen in FIGS. 34 and 35.

Prior to attachment of the anvil assembly 30 and the anvil retainer 38, the stapling device 10 is in the un-approximated position. In this position, the biasing member 106 (FIG. 2) in engagement with the coupling member 86 urges the pusher link 74 to its proximal-most position in which the coupling member 86 abuts the screw-stop 306, and the biasing member 512 is in engagement with the slide member 500 (FIG, 2) of the indicator mechanism to position the slide member 500 in engagement with the projection 518 (FIG. 23) of the indicator 24 to pivot the indicator 24 in a clockwise direction, as viewed in FIGS. 2 and 23. Additionally, the biasing member 549 (FIG. 23) is in engagement with the body 536 of the lockout member 530 to urge the lockout member 530 to its distal-most position, wherein the lip portion 542 of the lockout member 530 is positioned above the extension 26B (FIG. 2) of the trigger lock 26 to prevent movement of the trigger lock 26 to the unlocked position. The biasing member 82A (FIG. 2) is also engaged with the pivot member 79 to urge the pivot member 79 to the base of the vertical slot 82 formed between the handle sections 19A, 19B, and the tactile indicator 580 is in the retracted or downward position with the protrusion 580A positioned with the detent 582A.

To attach the anvil assembly 30 to the anvil retainer 38, the center rod 154 (FIGS. 8, 9) of the anvil assembly 30 is positioned within the anvil retainer 38 (FIGS. 1 and 5), and advanced proximally such that the annular protrusion 280 of the center rod 154 engages the flexible fingers 272 of the anvil retainer 38. Upon engagement of the annular protrusion 280 with the flexible fingers 272, the flexible fingers 272 are forced outwardly, thereby facilitating engagement of the annular protrusion 280 and the annular recess 282 of the anvil retainer 38 to inhibit relative longitudinal movement between the center rod 154 and the anvil retainer 38.

Following attachment of the anvil assembly 30 and the anvil retainer 38 (FIG. 1), the stapling device 10 can be moved into the approximated position. To do so, approximation knob 22 is rotated to move the anvil assembly 30 proximally towards the shell assembly 31 as rotation of the approximation knob 22 causes corresponding rotation of the cylindrical sleeve 33, which thereby moves the pin 52 (FIG. 2) along the helical channel 50. Movement of the pin 52 along the helical channel 50 causes the screw 32 to translate proximally within the sleeve 33. As the distal end of the screw 32 is operatively connected to the anvil retainer 38, retraction of the screw 32 within the sleeve 33 is translated into proximal movement of the anvil retainer 38, and consequently, the connected anvil assembly 30. During proximal movement of the anvil assembly 30, the target tissue is drawn into the shell assembly via the attachment between the suture "S" and the center rod 154 at the apertures 286A-286C. (FIGS. 35, 36)

Since the screw stop 306 is connected to the screw 32 by the set screw 312 (FIG. 2), retraction of the screw 32 within sleeve 33 causes the screw stop 306 to move from a distal position within the stationary handle 18 to a proximal position. During this movement, the first engagement member 522 formed on the screw stop 306 abuts the proximal end 506a of the slot 506 of the slide plate 500, and moves the slide plate 500 proximally against the bias of the spring 512. As the slide plate 500 moves proximally, the lip 508 of the slide member 500 engages the projection 520 (FIG. 23) on the indicator 24 to pivot the indicator 24 in a counter-clockwise direction, as viewed in FIGS. 2 and 23.

As the screw stop 306 is moved from the distal position to the proximal position, the second engagement member(s) 548 (FIG. 20) of the screw stop 306 come into engagement with the distal legs 540A (FIG. 24) of the lockout member 530 to move the lockout member 530 proximally to a position in which the lip portion 542 is spaced proximally from the extension 26B (FIG. 2) of the trigger lock 26. In this position, the trigger lock 26 can be pivoted to an unlocked position to permit firing of the stapling device 10.

As the screw stop 306 is moved into its proximal-most position within the stationary handle 18, the abutment surface 307 of the screw stop 306 is positioned to engage the pivot member 79 (FIG. 2) of the firing link 72. The abutment surface 307 engages the pivot member 79 during firing of the stapling device 10, and acts as a backstop for the pivot member 79.

During firing of the surgical stapling device 10, as the trigger 20 is compressed towards the stationary handle 18, the pivot member 79 (FIG. 2) engages the abutment surface 307 (FIG. 18) on the screw stop 306, and the firing trigger 20 is pushed distally. Since the distal end of the firing trigger 22 is connected to the proximal end of pusher link 74 through the coupling member 86, distal movement of the firing trigger 20 causes corresponding movement of the pusher link 74 to effectuate advancement of the pusher back 186 (FIG. 4) within the shell assembly 31 (FIG. 1). As the pusher back 186 is advanced within the shell assembly 31, the fingers 190 (FIG. 4) engage and eject the fasteners 230 (FIGS. 4 and 14) from the fastener guide 192. The knife 188 moves concurrently with pusher back 186 into engagement with the cutting ring 128 (FIG. 10) to thereby sever tissue "H" positioned between the anvil assembly 30 and the shell assembly 31, as seen in FIG. 36

As the trigger 20 is actuated, i.e., compressed towards the stationary handle 18, the extension 590 (FIG. 2) of the firing link 72 is pivoted towards, and into engagement with, the abutment member 580 (FIGS. 25, 26) to move the abutment member 580 from the retracted position to the extended position. In the extended position, the abutment member 580 obstructs the channel 111 formed in the stationary handle 18.

After firing of the device, the anvil assembly 30 (FIG. 1) is separated from the shell assembly 31. As the anvil assembly 30 is moved distally, the wings 584 (FIGS. 2, 20) of the screw stop 306 engage the tactile indicator 580 (FIG. 25), which thereby provides the clinician with a tactile and/or audible indication that center rod 154 (FIGS. 8, 19) can be disengaged from the anvil retainer 38 (FIG. 10).

FIGS. 12 and 12A illustrate an alternate embodiment of the surgical stapler of the present disclosure, designated generally by reference numeral 110. Stapler 110 includes a handle assembly 112, a central body portion 114 and a shell assembly 120. Surgical stapler 110 is identical to stapler 10 of FIG. 1 except for the alignment pins and shell assembly receiving holes described below and thus the internal components are not shown or described.

Anvil head 166 has a plurality of projections shown in the form of alignment pins 171 engagable with alignment holes 121 in the shell assembly 120. The pins or projections 171 extend proximally from the anvil head 166 and function to help align the anvil 166 and shell assembly 120 and to limit axial movement of the anvil head, especially in the instance where a relatively long anvil shaft is provided such as in hemorrhoid staplers. It should be appreciated that the alignment pins can also be utilized in other circular staplers. The pins 171 can have tapered ends 173 as shown in FIG. 12A.

The pins function to limit movement of the anvil head 166 with respect to the shell assembly 120. In one embodiment, the pins have an outer dimension substantially equal to the inner diameter of the alignment holes of the shell assembly 120 to frictionally fit within the alignment holes with sufficient force for retention, while not inhibiting re-approximation of the anvil assembly. In other embodiments, the pins can have a smaller outer dimension in relation to the inner diameter of the alignment holes to thereby more loosely be seated in the alignment holes, while still functioning to limit axial movement and rotational movement of the anvil head. The pins 171 are preferably inboard (radially inward) of the circular knife and the staple rows of the stapler 110. Two or more pins substantially equally radially spaced are provided in the illustrated embodiment. The pins can be spaced at intervals other than the approximately 180 degrees shown. Although the pins are shown with an anvil shaft 164 having through holes 175 for a purse string suture, the pins can be used with other anvil shafts.

Figures 27, 28:
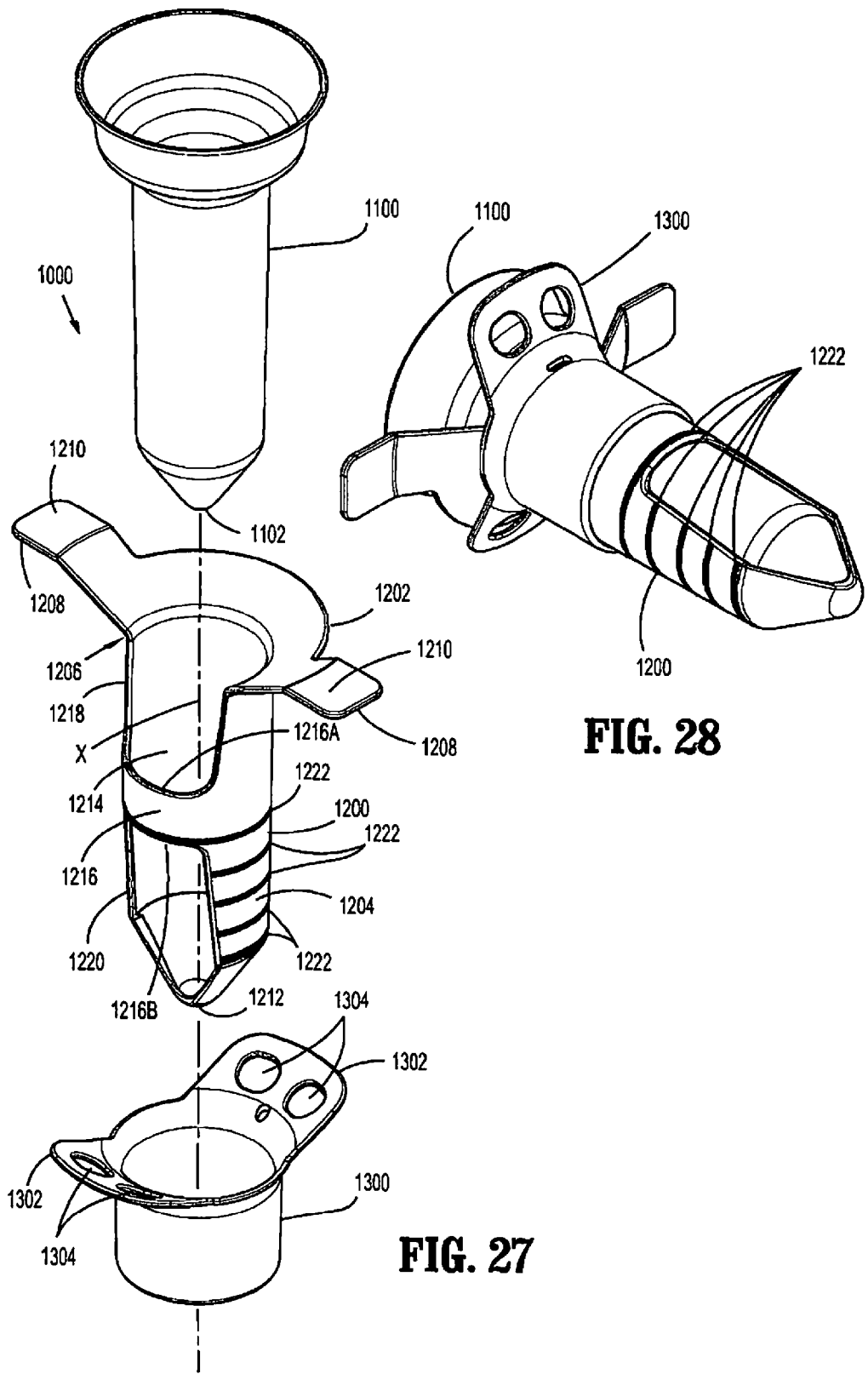
FIG. 27 is a front, perspective view of an anoscope kit including an obturator, an anoscope, and a port for use with the surgical stapling device.
FIG. 28 is a side, perspective view of the assembled anoscope kit.
Figure 29:
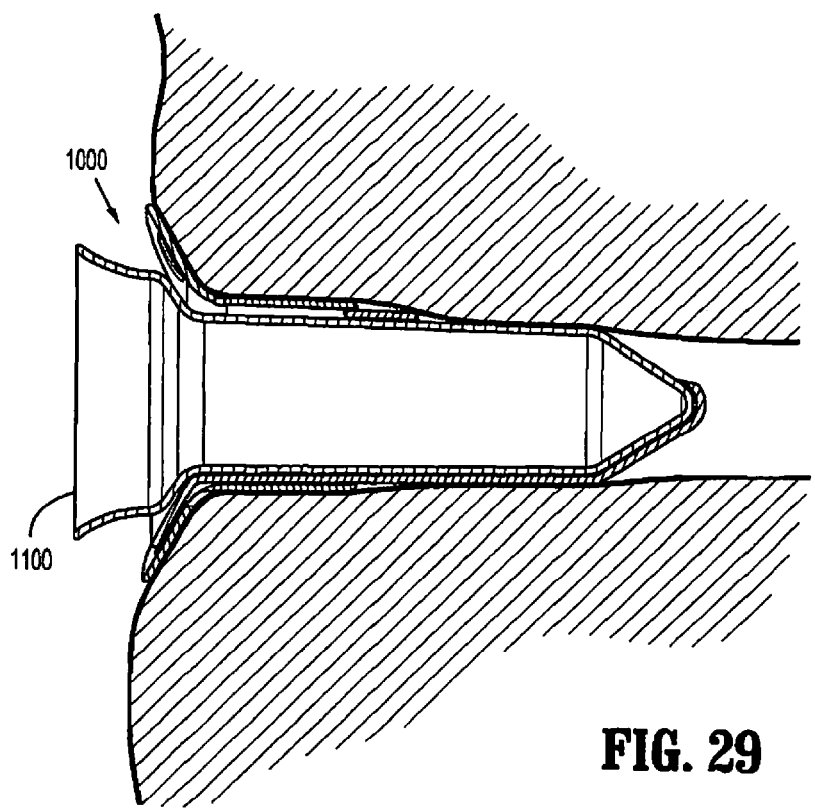
FIG. 29 is a longitudinal cross-sectional view of the assembled anoscope kit positioned within a patient.

With reference now to FIGS. 27 and 28, an anoscope kit 1000 is illustrated for use with the aforedescribed stapling device 10 (FIG. 1). The anoscope kit 1000 facilitates access to internal tissue during the course of a surgical procedure. For example, during the following discussion, the anoscope kit 1000 and the stapling device 10 will be discussed in the context of a surgical hemorrhoidal procedure, wherein hemorrhoidal tissue "H" (FIG. 35) is removed from a patient's anal canal. Note the stapling device 10 disclosed herein can be used with other anoscope kits or with other ports, or inserted directly into the body opening.

The anoscope kit 1000 includes an obturator 1100 with a dilating tip 1102, an anoscope 1200, and a port 1300. In one embodiment of the anoscope kit 1000, it is envisioned that the anoscope 1200 and the port 1300 may be composed of a clear material, e.g., polycarbonate, to facilitate the visualization of target tissue, as well as any adjacent or surrounding tissue, during the surgical procedure. However, alternative materials of construction can also be utilized.

The anoscope 1200 includes a dished flange 1202, and a sleeve 1204 that extends along a longitudinal axis "X." The flange 1202 extends from a proximal end 1206 of the sleeve 1204, and includes a first pair of wings 1208 that extend radially outwardly therefrom relative to the longitudinal axis "X." The wings 1208 are configured and dimensioned for manual engagement by the clinician to facilitate manipulation of the anoscope 1200 during the course of the surgical hemorrhoidal procedure. The wings 1208 preferably include a substantially uniform proximal surface 1210, however it could alternatively include a textured surface.

The sleeve 1204 of the anoscope 1200 extends distally from the flange 1202, and defines an internal dimension that allows for removable reception of the obturator 1100. The sleeve 1204 includes a substantially conical distal tip 1212 to facilitate the dilation of tissue, e.g., the patient's anal canal, and thus, insertion of the anoscope 1200, as well as rotation of the anoscope 1200 once positioned internally.

To assist in placement of purse strings, the sleeve 1204 may include markings 1222. When included, the markings 1222 facilitate the placement of purse strings at a constant depth within the anal canal.

The sleeve 1204 further includes an open region 1214 that extends longitudinally therethrough along the axis "X," and a bridge 1216 that spans the open region 1214, thereby dividing the open region 1214 into respective proximal and distal openings 1218, 1220. It is envisioned that the bridge 1216 may extend across the sleeve 1204 to define any arc of suitable dimensions. For example, it is envisioned that the arc defined by the bridge 1216 may be less than 180°. However, an arc greater than 180° is also contemplated.

The configuration of the bridge 1216 may be altered or varied in alterative embodiments to realize any suitable axial length. In one particular embodiment, the bridge 1216 defines an axial length of about 1.5 cm (approximately 0.59 inches), and is positioned such that respective proximal and distal ends 1216A, 1216B of the bridge 1216 are respectively located about 3 cm (approximately 1.18 inches) and about 4.5 cm (approximately 1.77 inches) from the proximal end 1206 of the sleeve 1204, i.e., from the point where the flange 1202 extends radially from the sleeve 1204. In this embodiment, upon insertion of the anoscope 1200 into the patient's anal canal, the distal opening 1220 will be positioned above the dentate line, which is located in the human anal canal about 2 cm (approximately 0.78 inches) from the anus, so that purse stringing, and subsequent tissue removal, e.g., by the stapling device 10 of FIG. 1, will also occur above the dentate line.

The port component 1300 of the anoscope kit 1000 defines an internal dimension that allows for removable reception of the anoscope 1200, and includes a pair of wings 1302 that extend outwardly therefrom relative to the longitudinal axis "X". The wings 1302 are configured and dimensioned for manual engagement by the clinician to facilitate handling and manipulation of the port 1300 during the course of the hemorrhoid procedure. To facilitate fixation of the port 1300, the wings 1302 may include a pair of apertures 1304 that are configured and dimensioned to receive a flexible member (not shown), such as a suture, that can be secured to the patient's tissue.

With reference now to FIGS. 29-37 as well, the use and operation of the anoscope kit 1000 in connection with the stapling device 10 of FIG. 1 will now be discussed. Prior to insertion, the anoscope kit 1000 is assembled as illustrated in FIG. 28. Specifically, the anoscope 1200 is positioned coaxially within the port 1300, and the obturator 1100 is positioned coaxially within the sleeve 1204 of the anoscope 1200. The assembled anoscope kit 1000 is then inserted transanally into a patient (FIG. 29) such that the bridge 1216 is positioned above the dentate line. Thereafter, the obturator 1100 is removed, leaving the anoscope 1200 positioned within port 1300, which extends from the patient's anus (FIG. 30). Either prior or subsequent to assembly of the anoscope kit 1000, the port 1300 may be optionally fixed to the patient's tissue by the aforementioned flexible member (not shown). To reiterate, the flexible member (e.g. suture) can be positioned within the apertures 1304 included on the wings 1302 of the port 1300, and can be thereafter secured to the patient.

Figure 31:
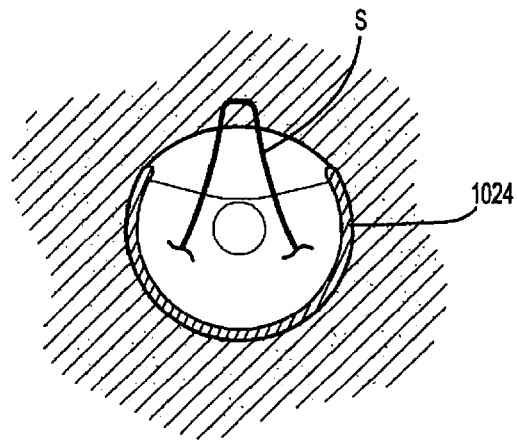
FIGS. 31-33 are proximal end views of the anoscope kit positioned within a patient following removal of the obturator illustrating a purse stringing procedure in which a suture is attached to target tissue.
Figure 32:
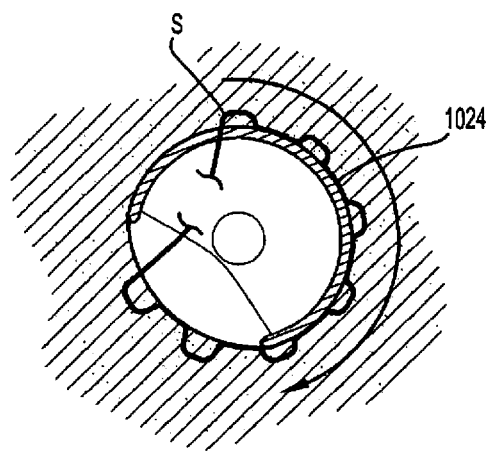
Figure 33:
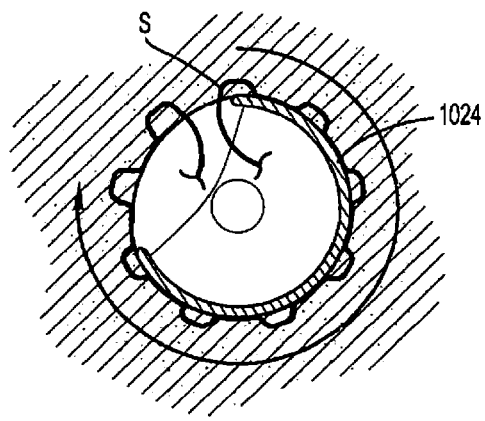

As seen in FIGS. 31-33, following removal of the obturator 1100, the target tissue, such as internal hemorrhoidal tissue "H" (FIG. 35), is received by the distal opening 1220 (FIGS. 27, 30) in the sleeve 1204 such that the tissue is positioned within the sleeve 1204 of the anoscope 1200. The clinician then attaches a length of suture "S" to the target tissue "H," a procedure referred to generally as "purse stringing." Thereafter, the anoscope 1200 (FIG. 27) can be rotated within the port 1300 to one or more subsequent positions, exemplified in the transition between FIGS. 31, 32, and 33, such that additional internal hemorrhoidal tissue, if any, can be received within the distal opening 1220 (FIGS. 27, 30) and sutured, or purse stringed.

After purse stringing is completed, the anoscope 1200 (FIG. 27) is removed from the patient's anus. The anvil assembly 30 of the stapling device 10 of FIG. 1 is then inserted into the patient's anal cavity, and the two ends of the suture "S" are passed through one of the apertures 286A-286C formed in the center rod 154, as shown in FIG. 34, dependent upon the amount of tissue the clinician wishes to draw into the shell assembly 31. The length of the suture "S" is such that the suture "S" extends from the port 1300 after positioning within the apertures 286A-286C (FIG. 34).

Figure 37:
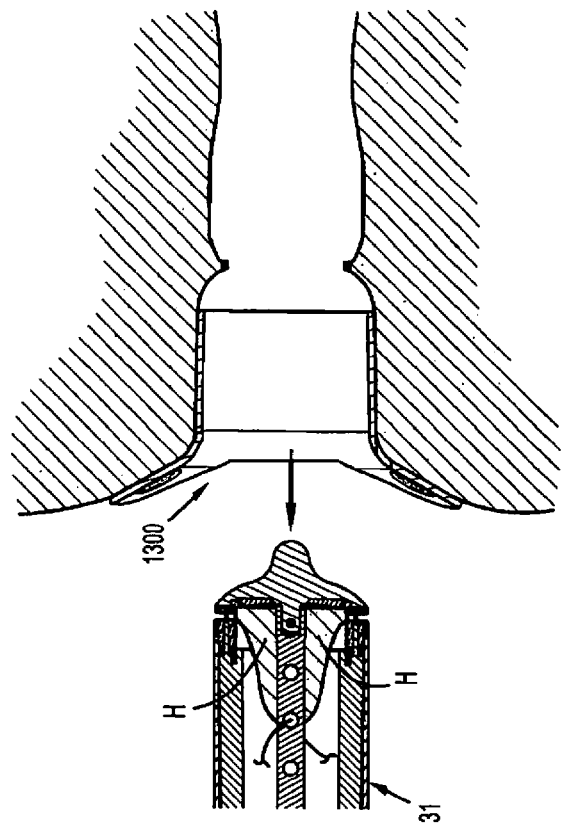
FIG. 37 is a longitudinal cross-sectional view of the surgical stapling device following removal of the surgical stapling device and attached anvil assembly from the port component of the anoscope kit, and illustrating the removed target tissue within the shell assembly of the stapling device.

The anvil assembly 30 is then connected to the anvil retainer 38 (FIG. 35) in the manner discussed above, and the approximation knob 22 (FIG. 1) is rotated to move the anvil assembly 30 proximally, i.e., towards, the shell assembly 31, such that the target tissue "H" is positioned within the shell assembly 31, The stapling device 10 is then fired to sever and fasten the target tissue "H." After severing of the tissue "H," the stapling device 10 can be removed from the port 1300 with the tissue "H" positioned within the shell boss 31, as shown in FIG. 37.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A surgical fastener applying apparatus comprising:
   an elongated body member having proximal and distal ends; and
   a fastener applying portion disposed adjacent the distal end of the elongated body member, the fastener applying portion comprising:
      a first member defining a central opening, and including an annular first tissue contacting surface, the first tissue contacting surface comprising:
         a plurality of slots through which a plurality of surgical fasteners are ejected during firing of the surgical fastener applying apparatus; and
         an alignment depression, wherein the alignment depression is spaced apart from the plurality of slots and spaced apart from the central opening; and
      a second member movable in relation to the first member, the second member including an annular second tissue contacting surface and a fixed projection extending therefrom, wherein the fixed projection frictionally fits within the alignment depression of the first tissue contacting surface to inhibit relative axial displacement between the first and second members.

2. The surgical stapler according to claim 1, wherein the first tissue contacting surface includes a plurality of alignment depressions, and the second tissue contacting surface includes a plurality of projections extending therefrom in registration with the plurality of alignment depressions.

3. The surgical stapler according to claim 2, wherein the plurality of alignment depressions are spaced equidistant from one another, and the plurality of projections are spaced equidistant from one another.

4. The surgical stapler according to claim 1, wherein at least one alignment depression of the plurality of alignment depressions in the first tissue contracting surface is a hole extending substantially through the first tissue contacting surface.

5. The surgical stapler according to claim 1, wherein at least one projection of the plurality of projections includes a tapered end.

6. The surgical stapler according to claim 1, wherein the second tissue contacting surface includes a plurality of pockets configured and dimensioned to receive the surgical fasteners to facilitate formation thereof.

7. The surgical stapler according to claim 1, wherein the plurality of alignment depressions in the first tissue contacting surface are spaced radially inward of the plurality of slots formed in the first tissue contacting surface, and radially outward of the central opening.

8. A surgical fastener applying apparatus comprising:
an elongated body member having proximal and distal ends; and
a fastener applying portion disposed adjacent the distal end of the elongated body member, the fastener applying portion comprising:
a first member defining a central opening, and including a first tissue contacting surface, the first tissue contacting surface comprising:
a plurality of slots through which a plurality of surgical fasteners are ejected during firing of the surgical fastener applying apparatus; and
a second member movable in relation to the first member, the second member including a second tissue contacting surface, wherein the first tissue contacting surface includes a plurality of alignment depressions, and the second tissue contacting surface includes a plurality of projections extending therefrom, wherein the plurality of projections frictionally fit within the plurality of alignment depressions, wherein the plurality of alignment depressions are spaced equidistant from the central opening.

9. A fastener applying portion for use with a surgical fastener applying apparatus, the fastener applying portion comprising:
a first member defining an annular first tissue contacting surface with a plurality of fastener slots formed therein, the first tissue contacting surface having an alignment depression formed therein spaced apart from the plurality of slots; and
a second member movable in relation to the first member, the second member including an annular second tissue contacting surface, and an alignment protrusion fixedly extending therefrom, wherein the alignment protrusion frictionally fits within the alignment depression in the first tissue contacting surface to inhibit relative axial displacement between the first and second members.

10. The fastener applying portion according to claim 9, wherein the first tissue contacting surface includes a plurality of alignment depressions spaced equidistant from one another, and the second tissue contacting surface includes a plurality of alignment protrusions extending therefrom in registration with the plurality of alignment depressions.

11. The fastener applying portion according to claim 10, wherein the plurality of alignment projections extending from the second tissue contacting surface are positioned in diametrical opposition, and the plurality of alignment protrusion in the first tissue contacting surface are positioned in diametrical opposition.

12. The fastener applying portion according to claim 9, wherein the second member further comprises a plurality of venting apertures.

13. The fastener applying portion according to claim 9, wherein the alignment protrusion extending from the second tissue contacting surface includes a tapered end.

14. The fastener applying portion according to claim 9, wherein the second tissue contacting surface further comprises a plurality of fastener forming pockets formed therein.

15. The fastener applying portion according to claim 9, wherein the alignment depression in the first tissue contacting surface is spaced radially inward of the plurality of slots formed in the first tissue contacting surface, and radially outward of the central opening in the first member.

16. The fastener applying portion according to claim 9, wherein the alignment depression is a hole extending entirely through the first tissue contacting surface.

17. A method of performing a surgical procedure comprising:
inserting a surgical fastener applying apparatus into an opening in a patient;
positioning the surgical fastener applying apparatus such that target tissue is positioned between first and second members comprising a fastener applying portion of the surgical fastener applying apparatus;
approximating the first and second members of the fastener applying portion such that a projection fixedly extending from an annular second tissue contacting surface of the second member frictionally fits within a corresponding alignment depression formed in an annular first tissue contacting surface of the first member to inhibit relative axial displacement between the first and second members, wherein the depression is spaced from a plurality of slots formed in the first tissue contacting surface of the first member, and from a central opening defined in the first member; and
firing the surgical fastener applying apparatus to eject a plurality of surgical fasteners through the plurality of slots formed in the first tissue contacting surface of the first member into the target tissue positioned between the first and second members of the fastener applying portion.

18. The method according to claim 17, wherein approximating the first and second members includes inserting a plurality of projections extending from the second tissue contacting surface of the second member into a corresponding plurality of alignment depressions formed in the first tissue contacting surface of the first member.

* * * * *